(12) United States Patent
Tanaka

(10) Patent No.: US 8,123,804 B2
(45) Date of Patent: Feb. 28, 2012

(54) INTRAOCULAR LENS INSERTION TOOL

(75) Inventor: Masayoshi Tanaka, Nagoya (JP)

(73) Assignee: Kowa Company, Ltd., Nagoya-shi (JP)

( * ) Notice: Subject to any disclaimer, the term of this patent is extended or adjusted under 35 U.S.C. 154(b) by 324 days.

(21) Appl. No.: 12/310,557

(22) PCT Filed: Aug. 8, 2007

(86) PCT No.: PCT/JP2007/000851
§ 371 (c)(1),
(2), (4) Date: Mar. 5, 2009

(87) PCT Pub. No.: WO2008/029498
PCT Pub. Date: Mar. 13, 2008

(65) Prior Publication Data
US 2010/0130985 A1 May 27, 2010

(30) Foreign Application Priority Data

Sep. 5, 2006 (JP) ................................ 2006-239870

(51) Int. Cl.
*A61F 2/16* (2006.01)
(52) U.S. Cl. ...................................... 623/6.12; 606/107
(58) Field of Classification Search .......... 606/107–108; 623/6.11–6.13, 6.18, 6.32, 6.45; 604/57, 604/59, 60
See application file for complete search history.

(56) References Cited

U.S. PATENT DOCUMENTS

| | | | | |
|---|---|---|---|---|
| 5,123,905 A | * | 6/1992 | Kelman | 606/107 |
| 5,873,879 A | * | 2/1999 | Figueroa et al. | 606/107 |
| 5,944,725 A | * | 8/1999 | Cicenas et al. | 606/107 |
| 5,947,975 A | | 9/1999 | Kikuchi et al. | |
| 5,947,976 A | * | 9/1999 | Van Noy et al. | 606/107 |
| 6,558,395 B2 | | 5/2003 | Hjertman et al. | |
| 7,276,071 B2 | * | 10/2007 | Lin et al. | 606/107 |
| 7,645,300 B2 | * | 1/2010 | Tsai | 623/6.12 |
| 2001/0007942 A1 | * | 7/2001 | Kikuchi et al. | 606/107 |
| 2002/0022881 A1 | * | 2/2002 | Figueroa et al. | 623/6.12 |

(Continued)

FOREIGN PATENT DOCUMENTS

CN 1402625 A 3/2003

(Continued)

OTHER PUBLICATIONS

Office Action issued in Chinese Patent Application No. 200780032887.0 dated Nov. 2, 2010 (with translation).

(Continued)

*Primary Examiner* — S. Thomas Hughes
*Assistant Examiner* — David Eastwood
(74) *Attorney, Agent, or Firm* — Oliff & Berridge, PLC

(57) ABSTRACT

An intraocular lens insertion tool of a novel structure, capable of easily and reliably placing an intraocular lens in a human eye. A placement part formed communicated with the base end of an insertion tube part is formed in a tool body. A placement surface for placing an intraocular lens thereon is formed on the placement part. Through-holes are formed in the portion where the placement surface is formed, and a carrying member is assembled from the outside to the portion where the placement surface is formed. Support parts formed projected from the carrying member are projected from the support surface through the through-holes. The intraocular lens is supported by projecting distal end faces of the support parts.

16 Claims, 16 Drawing Sheets

U.S. PATENT DOCUMENTS

| | | | |
|---|---|---|---|
| 2003/0036765 A1* | 2/2003 | Van Noy | 606/107 |
| 2004/0243141 A1 | 12/2004 | Brown et al. | |
| 2005/0049606 A1* | 3/2005 | Vaquero et al. | 606/107 |
| 2005/0182419 A1* | 8/2005 | Tsai | 606/107 |
| 2005/0222577 A1* | 10/2005 | Vaquero | 606/107 |
| 2009/0043313 A1 | 2/2009 | Ichinohe et al. | |

FOREIGN PATENT DOCUMENTS

| | | |
|---|---|---|
| JP | A 11-514278 | 12/1999 |
| JP | B2-3412103 | 6/2003 |
| JP | B2-3420724 | 6/2003 |
| JP | A 2004-351196 | 12/2004 |
| JP | B2-3665643 | 6/2005 |
| JP | A 2006-181269 | 7/2006 |
| WO | WO 2005/023154 A2 | 3/2005 |
| WO | WO 2006/080191 A1 | 8/2006 |

OTHER PUBLICATIONS

Oct. 5, 2011 Office Action issued in the Japanese patent application No. 2006-239870 (with translation).

* cited by examiner

INTRAOCULAR LENS INSERTION TOOL

TECHNICAL FIELD

The present invention relates to an intraocular lens insertion tool used to insert an intraocular lens into the eye.

BACKGROUND ART

One method employed in the past in the field of surgery for conditions such as cataracts involves extracting the intracapsular crystalline lens through a surgical incision made in ocular tissue such as the cornea (sclera) or anterior capsule section of the lens, and once the lens has been removed, inserting an intraocular lens serving as a replacement for the crystalline lens into the eye through the incision and arranging it within the capsule.

Particularly in recent years, methods that employ an intraocular lens insertion tool like those disclosed in Patent Citations 1 to 3 have come into widespread use. Where such an insertion tool is employed, the intraocular lens can be inserted into the eye without expanding the surgical incision that was made for the purpose of extracting the crystalline lens, thereby reducing the labor entailed in the surgical operation, as well as reducing the risk of post-surgical astigmatism or infection.

Most of the conventional insertion tools, including those disclosed in Patent Citations 1 to 3, are adapted to enclose the intraocular lens within the insertion tool by placing the intraocular lens in a recloseable hinged portion, and then closing the hinged portion to shut the intraocular lens inside.

However, in an insertion tool having such a construction, there is a risk that, when the hinged portion is closed to enclose the intraocular lens within the insertion tool, once the hand is released from the hinged portion the hinged portion will open inadvertently, allowing the intraocular lens to fall out. This created a need for an additional operation, performed after the hinged portion is closed, to secure the hinged portion in the closed state using a retaining member such as a sleeve.

An additional risk encountered in the process of closing the hinged portion to shut the intraocular lens inside was that the position of the intraocular lens would move slightly, so that it could not be imparted with initial deformation in the desired shape. If the intraocular lens is not correctly imparted with initial deformation, subsequent plunging out of the intraocular lens may not proceed smoothly, and in some instances the intraocular lens may be subjected to unnecessary force, with a risk of possible damage to the intraocular lens.

Patent Citation 1: Japanese Patent Publication 3412103
Patent Citation 2: Japanese Patent Publication 3420724
Patent Citation 3: Japanese Patent Publication 3665643

DISCLOSURE OF THE INVENTION

Problem the Invention Attempts to Solve

With the foregoing in view, it is one object of the present invention to provide an intraocular lens insertion tool of novel design whereby the intraocular lens enclosing operation can be carried out easily and reliably.

Means for Solving the Problem

The modes of the present invention addressed to solving the aforementioned problems will be discussed below. The constituent elements employed in the modes may be employed in any possible combination.

Specifically, a first mode of the present invention relates to an intraocular lens insertion tool including an tool body having generally tubular shape adapted to accommodate an intraocular lens positioned in an enclosed state therein, and a plunging member adapted to be inserted into the tool body from behind in an axial direction so that the intraocular lens is transported forward in the axial direction while experiencing slight deformation and pushed out through an insertion tube part disposed in an axial distal end part of the tool body in order to insert the intraocular lens within an eye, characterized in that: the tool body has a placement part communicating with a base end of the insertion tube part; a placement surface for placement of the intraocular lens is formed on the placement part, and at least one insertion hole is formed in the placement part at a site thereof where the placement surface has been formed; a carrying member is attached from an outside to a placement surface formation site; and at least one support part projected from the carrying member is passed through the insertion hole and arranged projecting up from the placement surface, with the intraocular lens being supported on a projecting distal end face of the support part.

In the insertion tool constructed according to the present mode, the intraocular lens can be placed on the placement surface by detaching the carrying member from the tool body to retract the support parts that were projecting up from the placement surface, so that they are no longer positioned above the placement surface. The intraocular lens can thereby be placed on the placement surface through the simple operation of detaching the carrying member from the tool body, and the intraocular lens placement operation can be carried out easily. Additionally, because the intraocular lens can be positioned in a stable manner at the prescribed location, the risk of deformation of the intraocular lens to unanticipated shape due to its shifting position, and of possible damage to the intraocular lens caused by such deformation, can be reduced as well.

No particular limitation is imposed on the method for attaching the carrying member to the tool body. For example, in another possible mode, mating parts adapted to mate with one another are formed respectively on the carrying member and on the tool body, and the carrying member is fastened through mating to the tool body. In a preferred mode, the fastening structure of the carrying member will be one whereby the support parts are formed such that their upper face shape becomes progressively larger as they are inserted further into the through-holes, and the carrying member is fastened to the tool body by ramming the support parts into the through-holes. With such an arrangement, the through-holes and the support parts can constitute the fastening mechanism for the carrying member, obviating the need to provide a separate fastening mechanism.

A second mode of the present invention provides an intraocular lens insertion tool according to the first mode, wherein the tool is adapted for use with an intraocular lens that includes a main body section having an optical region, and retaining parts that project peripherally outward from the main body section for the purpose of positioning the main body section within the eye, wherein the projecting distal end faces of the support parts contact the intraocular lens at locations away from the optical region of the main body section, with at least the one of the outside peripheral edge part of the main body section and the retaining parts being supported by the support parts.

In the insertion tool constructed according to the present mode, contact of the support parts with the optical region of the intraocular lens is avoided. Possible damage to the optical region caused by contact with the support parts can thus be prevented.

The intraocular lens for which the insertion tool constructed according to the present mode is adapted to be used may be an intraocular lens in which the main body section and the retaining parts are integrally formed, or an intraocular lens in which the main body section and the retaining parts are formed as separate elements.

A third mode of the present invention provides an intraocular lens insertion tool according to the second mode wherein a projecting height dimension of the support parts from the placement surface is established such that the optical region of the intraocular lens supported on the support parts will be spaced away from the placement surface.

With this arrangement, the optical region of the intraocular lens can be supported in a noncontact state with respect to the placement surface, not just with respect to the support parts. The risk of possible damage to the optical region of the intraocular lens due to contact with other components can thus be more effectively reduced.

A fourth mode of the present invention provides an intraocular lens insertion tool according to any one of the first to third modes wherein the placement surface is defined by a flat surface. By so doing, the intraocular lens can be supported more stably, the intraocular lens enclosing operation can be carried out more easily, and position shift of the intraocular lens can be reduced as well.

A fifth mode of the present invention provides an intraocular lens insertion tool according to any of the first to fourth modes wherein an introduction projection extending in the axial direction of the tool body and projecting upward, and adapted to deform the intraocular lens to upwardly convex shape, is formed in a widthwise center part of the base end of the insertion tube part.

With this arrangement, initial deformation can be imparted to the intraocular lens through contact of the intraocular lens with the introduction projection. The intraocular lens can thereby be guided smoothly within the insertion tube part while bringing about stable deformation thereof inside the insertion tube part. The present mode is more preferably employed concomitantly with the flat placement surface of the preceding fourth mode. Specifically, despite the fact that the flat placement surface does not readily impart initial deformation to the intraocular lens, it will be possible to consistently impart initial deformation to the intraocular lens by means of the introduction projection.

A sixth mode of the present invention provides an intraocular lens insertion tool according to the fifth mode wherein the introduction projections are provided as a pair of elements spaced apart by a prescribed distance in a direction perpendicular to the axial direction of the tool body, and the plunging member is guided in the axial direction of the tool body by the introduction projections.

With this arrangement, the intraocular lens can be stably imparted with initial deformation by the introduction projections, as well as inhibiting diagonal deflection of the plunging member with respect to the axial direction of the tool body, so that the plunging member can be guided stably in the axial direction. Plunging of the intraocular lens by the plunging member can thus take place in a more stable manner. As will be appreciated from the present mode, the introduction projection of the fifth mode is not limited to one in number, and may be provided in plural number.

A seventh mode of the present invention provides an intraocular lens insertion tool according to any one of the first to sixth modes wherein an aperture that opens to an outer side of the tool body is formed in the placement part, and a covering part adapted to cover the aperture is integrally formed with the tool body; and a guide projection that extends in the axial direction of the tool body and, with the aperture covered by the covering part, projects to a heightwise location approximately equivalent to an inside peripheral face of the base end of the insertion tube part is formed on the covering part on a face thereof opposing the placement part.

With this arrangement, by covering the placement part with the covering part it will be possible to prevent the intraocular lens from becoming dislodged, and it will be easier to enclose the intraocular lens and insert it into the eye. Additionally, contact of the intraocular lens with the environment can be minimized, providing excellent advantages in terms of hygiene as well. According to the present mode in particular, due to the provision of the guide projection, the heightwise location of the intraocular lens inside the placement part can be aligned with the heightwise location of the inside peripheral face of the insertion tube part, and pushing of the intraocular lens into the insertion tube part can take place in a more consistently smooth manner so that the risk of damage to the intraocular lens due to excessive force caused by catching of the intraocular lens or the like can be effectively reduced.

An eighth mode of the present invention provides an intraocular lens insertion tool according to the seventh mode wherein a plunging member guide part adapted to guide the plunging member in the axial direction of the tool body is integrally formed on the covering part on the face thereof opposing the placement part.

With this arrangement, deflection of the plunging member during plunging can be reduced, and the intraocular lens can be plunged in a more stable manner. Furthermore, by forming the plunging member guide part on the covering part, there will be no adverse effects on plunging of the intraocular lens, and there will be a higher degree of freedom in design of the plunging member guide part.

No particular limitation is imposed as to the specific shape etc. of the plunging member guide part, which may be established with reference to considerations such as the shape and size of the plunging member, as well as the shape of the covering part on which the plunging member guide part is formed, the shape of the placement part situated facing it, and so on. For example, deflection of the plunging member in the widthwise direction could be minimized by forming projecting parts such as projections or ribs sandwiching the plunging member from either side in the widthwise direction; a projecting part that projects from the covering part towards the placement surface could be provided, and the plunging member sandwiched from both the upper and lower sides by the projecting part and the placement surface to minimize deflection of the plunging member in the vertical direction; or these measures could be combined to minimize deflection of the plunging member in both the widthwise and vertical directions.

A ninth mode of the present invention provides an intraocular lens insertion tool according to the seventh or eighth mode wherein a lubricant injection hole permitting injection of a lubricant into the tool body from the outside of the tool body is formed passing through the covering part in the thickness direction.

With this arrangement, since lubricant can be injected inside the tool body while the placement part is covered, the lubricant can be injected easily while preventing the intraocular lens from becoming dislodged. Additionally, since lubricant can be injected without opening the placement part, contact of the intraocular lens with the environment can be minimized, providing excellent advantages in terms of hygiene as well.

A tenth mode of the present invention provides an intraocular lens insertion tool according to the any one of the first to ninth modes wherein the tool is provided with retaining means for retaining a distal end of the plunging member in a state positioned to a rear of the placement part in the axial direction of the tool body.

With this arrangement, the tool body and the plunging member can be handled as an integral unit, obviating the need for a procedure to insert the plunging member into the tool body. By so doing, during insertion of the intraocular lens into the eye, once the carrying member has been detached from the tool body, the intraocular lens can be inserted simply by the operation of plunging the plunging member, making the insertion procedure a simpler one.

An eleventh mode of the present invention provides an intraocular lens insertion tool according to any one of the first to tenth modes wherein a distal end edge of the plunging member is provided with a readily deformable deforming member adapted to be placed in contact against the intraocular lens.

With this arrangement, excessive force on the intraocular lens can be avoided during plunging of the intraocular lens, thus reducing the risk of damage to the intraocular lens and in particular to the delicate retaining parts. Moreover the deforming member, through induced deformation thereof, can effectively respond to shape changes occurring on the path from the placement part to the insertion tube part, making it possible for plunging of the intraocular lens to take place in a stable manner. Further, in instances where a lubricant is injected into the placement part, pressure can be exerted effectively on the lubricant by the deforming member, making it possible for the intraocular lens to be pushed along by this pressure so that the risk of damage to the intraocular lens can be more effectively reduced.

In the intraocular lens insertion tool according to the eleventh mode, in another preferred mode corresponding to a twelfth mode of the present invention, a pair of branched parts branched in "Y" configuration are formed at the distal end edge of the plunging member; and an elastic member having hollow tubular shape is arranged bowed with both ends of the elastic member fitting about the outside of the branched parts so that a generally loop-shaped deforming member is defined by the member.

In a thirteenth mode of the present invention, in an intraocular lens insertion tool according to any of the first to twelfth modes, a notch is formed at the distal end of the plunging member to define a prescribed gap between the plunging member and the inside peripheral face of the insertion tube part.

With this arrangement, during plunging of the intraocular lens, the risk of damage to the retaining parts due to becoming pinched between the plunging member and the inside peripheral face of the insertion tube part can be reduced. No particular limitation is imposed in regard to the specific shape of the notch, and an appropriate shape can be employed according to the judgment of the practitioner.

For example, in the intraocular lens insertion tool according to the thirteenth mode, in another preferred mode corresponding to a fourteenth mode of the present invention, the distal end of the plunging member is formed with a generally rod shape; and the notch is formed by cutting away an area somewhat to a rear of the distal end edge of the plunging member along a prescribed length dimension in the axial direction across an entire width of the distal end.

In the intraocular lens insertion tool according to the thirteenth mode, in another preferred mode corresponding to a fifteenth mode of the present invention, the distal end of the plunging member is formed with a generally rod shape; and the notch is formed by cutting away both widthwise ends of the distal end along a prescribed dimension in the axial direction from the distal end edge.

DESCRIPTION OF SYMBOLS

10: insertion tool; 12: tool body: 14: plunger; 20: stage; 26: intraocular lens; 29: aperture; 30: placement surface; 50: carrying member; 56: main body support part; 58: leg support part; 61: upper face; 64: upper end face; 66: through-hole; 68: through-hole; 70: nozzle part

BEST MODE FOR CARRYING OUT THE INVENTION

In order to provide a fuller understanding of the present invention, the embodiments of the invention will be described in detail below with reference to the accompanying drawings.

Figure 1:
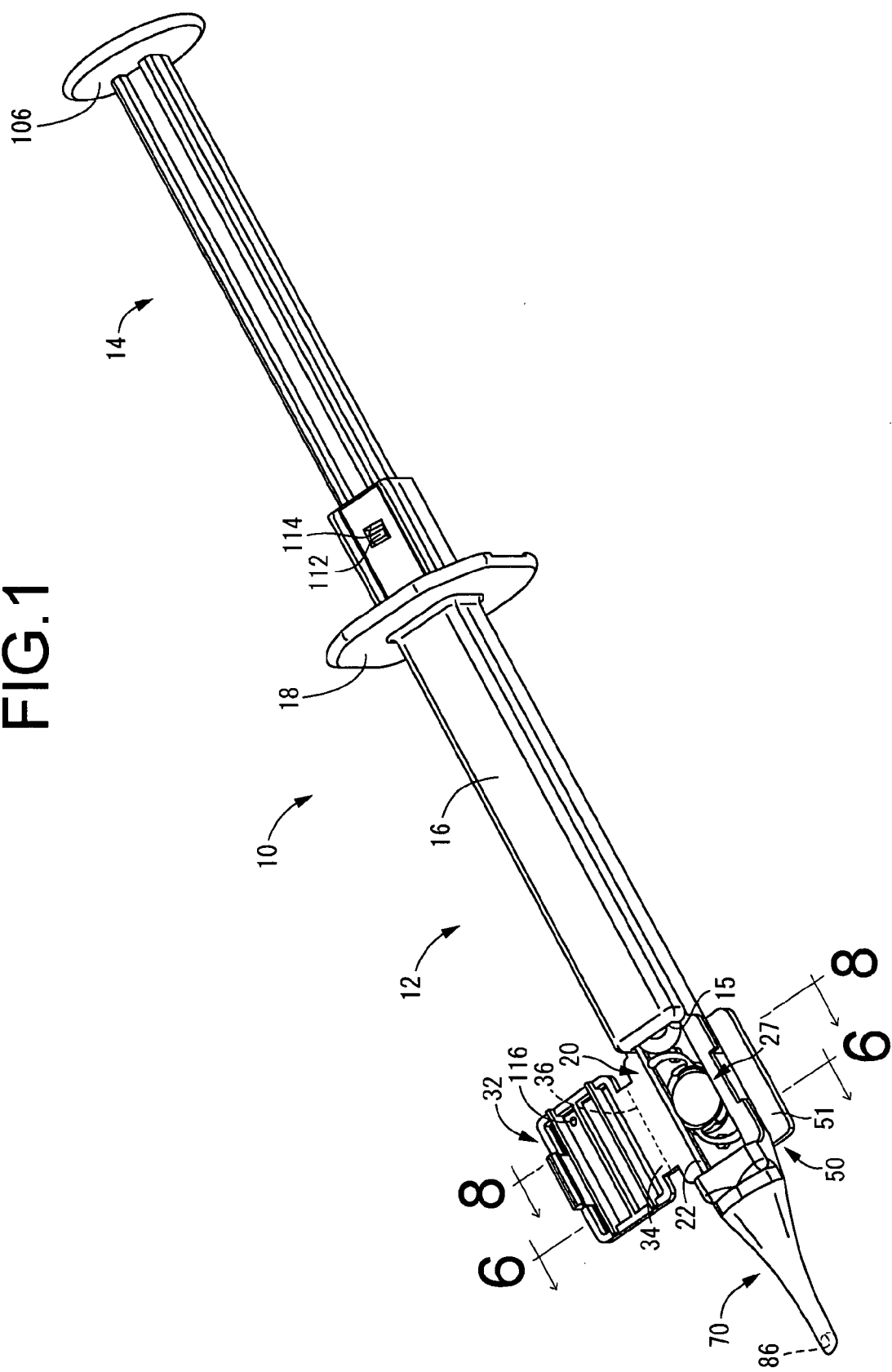
FIG. 1 Perspective view of an intraocular lens insertion tool according to a first embodiment of the present invention.

First, an intraocular lens insertion tool 10 according to a first embodiment of the present invention is depicted in FIG. 1. The insertion tool 10 is composed of a tool body 12 having generally tubular shape perforated through its interior along its entire length and open at the front and back ends, and into which inserts a plunger 14 provided as the plunging member. Herein, 'front' refers to the direction of extension of the insertion tool 10 (lower left in FIG. 1) and 'upward' refers to the upward direction in FIG. 1. 'Left-right direction' refers to the left-right direction of the insertion tool 10 in rear view (in FIG. 1, the lower right direction is left, and the upper left direction is right).

To describe in greater detail, the tool body 12 has a main tube part 16 of generally tubular shape. A through-hole 15 is formed passing through the interior of the main tube part 16 in the axial direction, with generally oblong cross section. A plate-like portion 18 that extends on the perpendicular to the direction of extension of the main tube part 16 is integrally formed at a location somewhat to the forward side from the back end of the main tube part 16.

Figure 2:
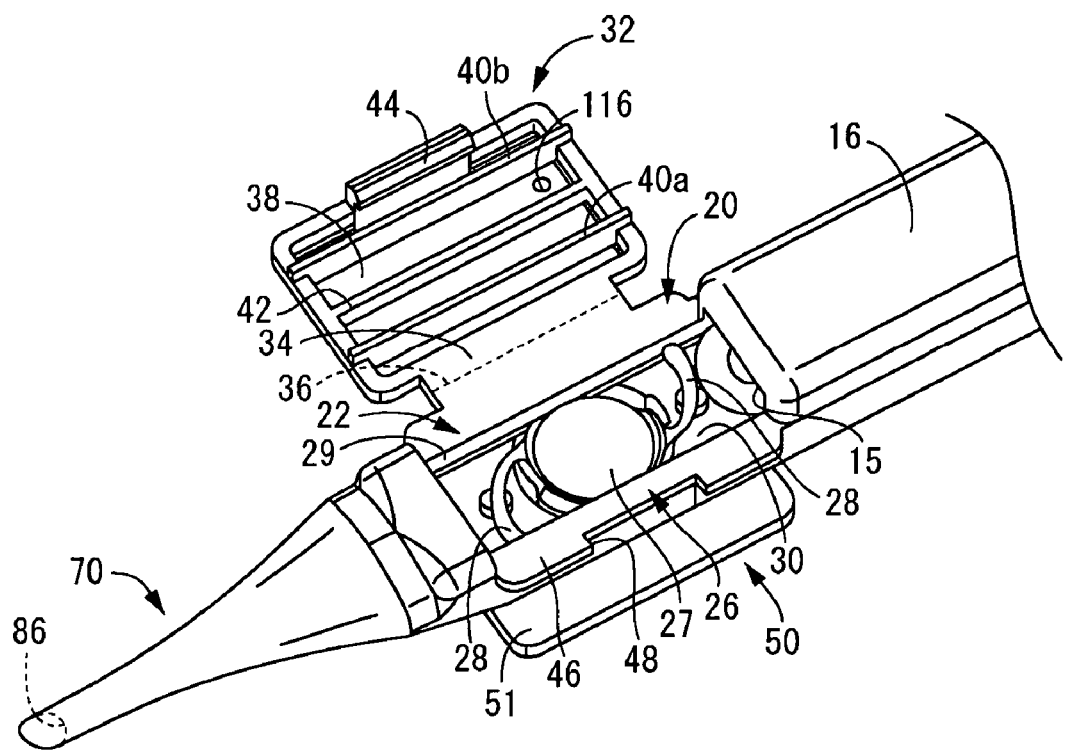
FIG. 2 Enlarged fragmentary perspective view of the insertion tool.

A stage 20 provided as the placement part is formed at the front of the main tube part 16 in the tool body 12. As depicted in FIG. 2, in the stage 20 there is formed a recessed slot 22 having width dimension slightly larger than the diameter dimension of the main body 27 of the intraocular lens 26 and extending in the axial direction. The recessed slot 22 has an axial length dimension somewhat larger than the maximum width dimension of the intraocular lens 26 inclusive of its retaining parts 28, 28.

Figure 3:
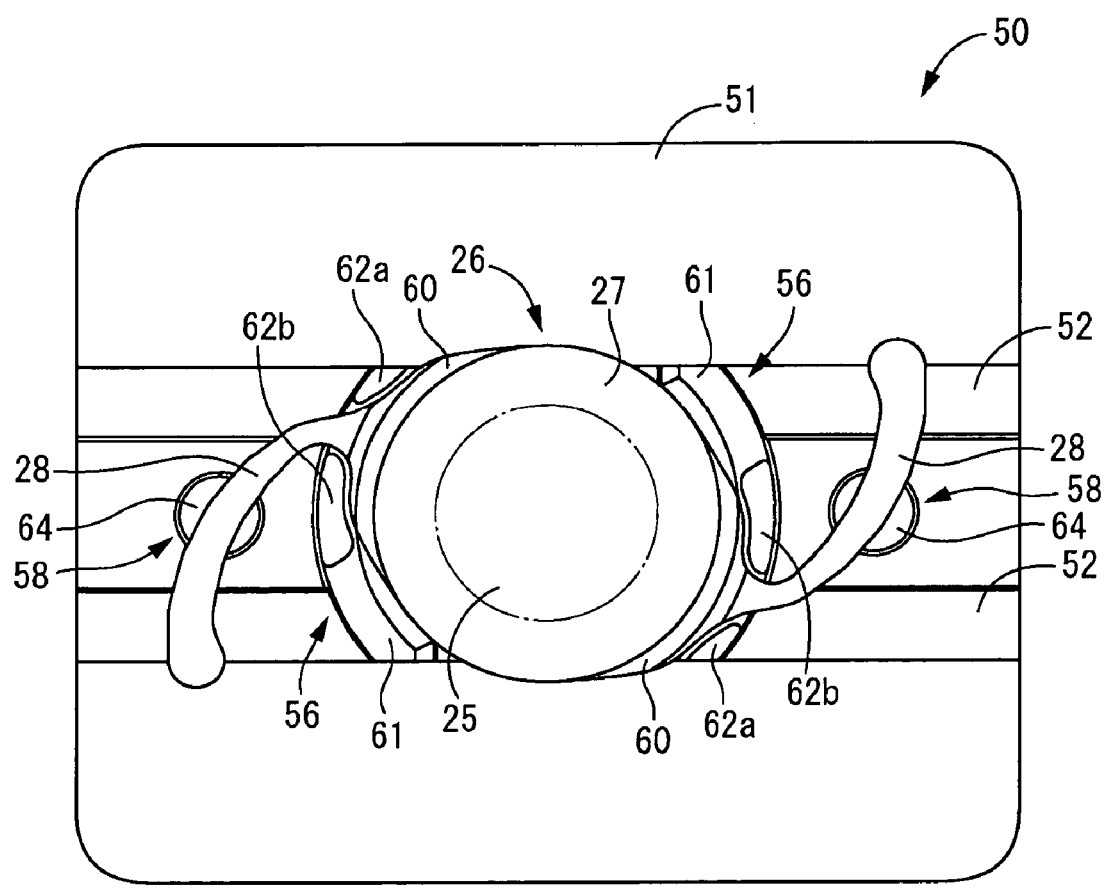
FIG. 3 Top view of a carrying member and an intraocular lens used with the insertion tool.

As depicted in FIG. 3, the intraocular lens 26 which is housed within the insertion tool 10 of the present embodiment has a main body 27, provided as the main body section, which includes an optical region 25; and a pair of retaining parts 28, 28 that project peripherally outward from the main body 27 and are adapted to position the main body 27 within the eye. The intraocular lens 26 of the present embodiment in particular is an intraocular lens whose main body 27 and retaining parts 28, 28 are integrally formed by the same component. While the insertion tool 10 of the present embodiment is favorably employed with intraocular lenses of this kind, it can of course be employed with intraocular lenses in which the main body 27 and the retaining parts 28, 28 are different components, for example.

The recessed slot 22 has an aperture 29 that opens upward, and its base face constitutes a placement surface 30. The placement surface 30 is defined by a flat face of width dimension slightly larger than the minimum width dimension (the vertical dimension in FIG. 3) of the intraocular lens 26, and an axial length dimension that is larger than the maximum width dimension (the left-right dimension in FIG. 3) of the intraocular lens 26. The heightwise position of the placement surface 30 is such that it is situated slightly above the heightwise position of the base face of the through-hole 15 in the main tube part 16; while at the front end edge of the through-hole 15 in the main tube part 16 there is formed a wall part 31 that extends up from the base face of the through-hole 15 and connects with the back end edge of the placement surface 30 (see FIG. 7). With this arrangement, the recessed slot 22 will communicate with the through-hole 15, and the width dimension of the recessed slot 22 will be approximately equal to the width dimension of the through-hole 15.

To one side of the aperture 29 (in the present embodiment, the right side), a cover part 32 provided as the covering part is integrally formed with the tool body 12. The cover part 32 has an axial dimension approximately equal to the axial dimension of the aperture 29, and a width dimension somewhat greater than the width dimension of the aperture 29. The cover part 32 is linked to the tool body 12 by a linking part 34 of generally thin plate shape formed by extending the upper end edge of the aperture 29 to one side (in the present embodiment, the right side). The linking part 34 has its minimum thickness in a bending part 36 that extends through its widthwise approximately center section in the axial direction of the tool body 12, and is adapted to bend at this bending part 36.

The cover part 32 can thereby be superposed over the aperture 29 by bending the linking part 34.

On the opposed face 38 of the cover part 32 facing towards the placement surface 30 there are integrally formed projecting left and right guide plate parts 40a, 40b provided as the pair of guide projections and extending in the axial direction of the tool body 12. These left and right guide plate parts 40a, 40b are formed along the entire axial extension of the cover part 32, with the distance between their opposing faces being somewhat smaller than the width dimension of the recessed slot 22. The outside peripheral edges of the opposed face 38 are somewhat thicker about its entire perimeter. In the present embodiment, the left and right guide plate parts 40a, 40b project out beyond these thick outside peripheral edges. At a location at the approximately center of the opposed face 38 between the left and right guide plate parts 40a, 40b there is integrally formed a center guide plate part 42, provided as the guide projection, which extends in the axial direction of the tool body 12 and parallel to the left and right guide plate parts 40a, 40b. In the present embodiment, the center guide plate part 42 has a height dimension equal to that of the thick outside peripheral edges of the opposed face 38, and is integrally formed extending from the outside peripheral edges, with a dimension such that it spans the distance between opposed outside peripheral edges in the axial direction.

A projecting catch piece 44 is formed on the edge of the cover part 32 on the side thereof opposite from the linking part 34, while an outwardly projected projecting edge part 46 is formed at the upper end edge of the aperture 29 on the side thereof opposite from the cover part 32. A catch notch 48 is formed in the projecting edge part 46 at a location corresponding to this catch piece 44.

Figure 4:
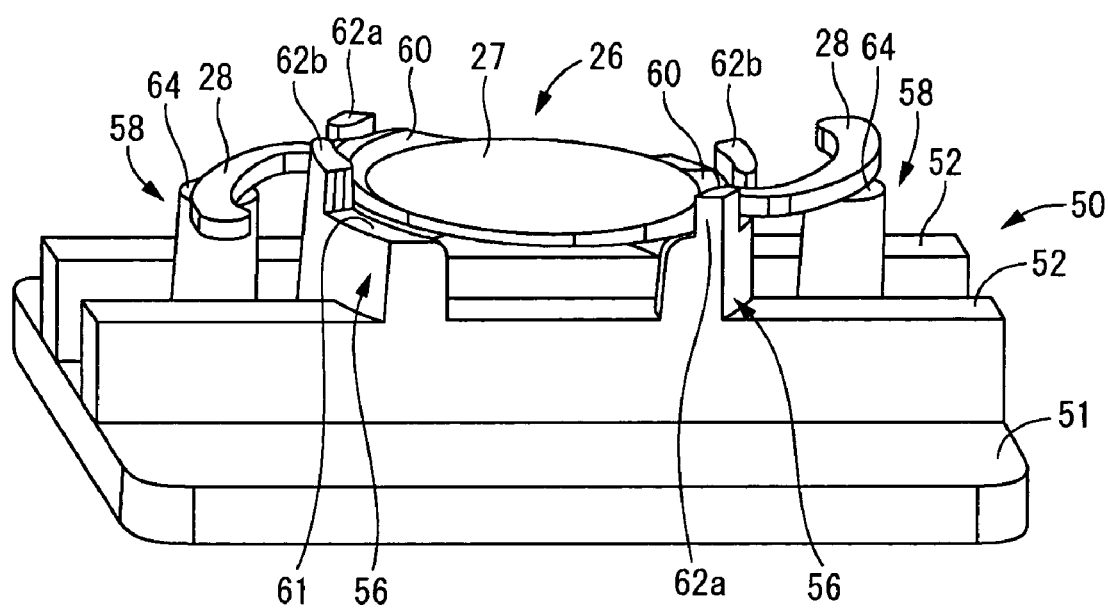
FIG. 4 Perspective view of the carrying member and the intraocular lens.

A carrying member 50 is detachably disposed to the lower side of the placement surface 30 of the stage 20 having the above construction. As depicted in FIGS. 3 and 4, the carrying member 50 is constituted as a separate member from the tool body 12, and includes a pair of positioning plate parts 52, 52, main body support parts 56, 56, and leg support parts 58, 58 that have been integrally formed with a plate part 51 of generally oblong plate shape and project upward. In FIGS. 3 and 4, in order to aid understanding, the carrying member 50 is depicted with the intraocular lens 26 placed thereon. In the following description relating to the carrying member 50, the longitudinal direction of the carrying member 50 refers to the direction of array of the main body support parts 56, 56 and the leg support parts 58, 58 (in FIG. 3, the left-right direction), while the width direction of the carrying member 50 refers to the direction perpendicular to the direction of array of the main body support parts 56, 56 and the leg support parts 58, 58 (in FIG. 3, the vertical direction).

The positioning plate parts 52, 52 are defined as a pair of plate-shaped elements situated to either side of the widthwise center part of the plate part 51 and extending approximately parallel across the entire length of the plate part 51 in its longitudinal direction. The widthwise distance separating the outside peripheral faces of the positioning plate parts 52, 52 is slightly smaller than the diameter dimension of the main body 27 of the intraocular lens 26.

The pair of main body support parts 56, 56 are formed so as to project upward from the approximately center part of the plate part 51. Seen in top view, the main body support parts 56, 56 are generally arcuate in shape having width dimension that spans the two outside peripheral faces of the positioning plate parts 52, 52, as well as having a curvature radius somewhat greater than that of the main body 27 of the intraocular lens 26; they also project upward from the plate part 51 and the positioning plate parts 52, 52. The main body support parts 56, 56 have progressively slightly increasing width dimension towards the bottom. The distance separating the main body support parts 56, 56 in the longitudinal direction is slightly greater than the distance separating the base ends 60, 60 of the retaining parts 28, 28 that connect with the main body 27 in the diametrical direction of the intraocular lens 26. Due to this arrangement, the intraocular lens 26 will be supported with its base ends 60 placed on the upper faces 61 of the main body support parts 56, so as to be supported without the main body 27 coming into contact with the carrying member 50, and in a non-deformed state.

Furthermore, at a first circumferential end of the upper face 61 of the main body support part 56 there are formed an outside projecting piece 62a and an inside projecting piece 62b, provided as positioning projections, that project further upward from the upper face 61. Of these projecting pieces 62a, 62b, the outside projecting piece 62a is formed at the outside end in the circumferential direction of the main body support part 56, while the inside projecting piece 62b is formed to the inward side of the outside projecting piece 62a and spaced apart from it by a prescribed distance in the circumferential direction of the main body support part 56. In this instance, the distance separating the outside projecting piece 62a and the inside projecting piece 62b in the circumferential direction of the main body support part 56 will be somewhat greater than the width dimension of the section of the retaining part 28 that extends out from the base end 60. The inside wall surfaces of the outside projecting piece 62a and the inside projecting piece 62b are curved to conform to the shape of the outside peripheral edge part of the base end 60.

Thus, the retaining parts 28 of the intraocular lens 26 which has been placed on the main body support parts 56 will extend between projecting pieces 62a, 62b and to the outward side from the main body support parts 56. These projecting pieces 62a, 62b will prevent the retaining parts 28 from rotating in the circumferential direction so that the intraocular lens 26 is positioned in the circumferential direction. In this instance, as depicted in FIG. 3, the intraocular lens 26 will be positioned so that as to minimize its projected area in the direction of extension of the positioning plate parts 52.

Furthermore, the pair of leg support parts 58, 58 are disposed spaced some distance outwardly from the main body support parts 56, 56 at generally medial locations between the opposing faces of the positioning plate parts 52, 52. The leg support parts 58, 58 have generally round post shape projecting upward from the plate part 51, and their upper end faces 64 are defined by flat faces situated at approximately the same heightwise location as the upper faces 61 of the main body support parts 56. The leg support parts 58, 58 have diameter dimension that progressively becomes slightly larger going from the upper end face 64 towards the plate part 51. The extending sections of the retaining parts 28 that extend outwardly beyond the main body support parts 56, 56 will be placed on the upper end faces 64 of the leg support parts 58.

Through this arrangement, the intraocular lens 26 is supported at the base ends 60 of its retaining parts 28 by the upper faces 61, 61 of the main body support parts 56, 56 while the extending sections of the retaining parts 28 are supported by the upper end faces 64, 64 of the leg support parts 58, 58. Thus, in the present embodiment, the main body support parts 56, 56 and the leg support parts 58, 58 constitute the support parts. The upper faces 61. 61 and the upper end faces 64, 64 constitute the projecting distal end faces of the support parts; and the intraocular lens 26 is supported at regions other than the optical region 25.

Figure 5:
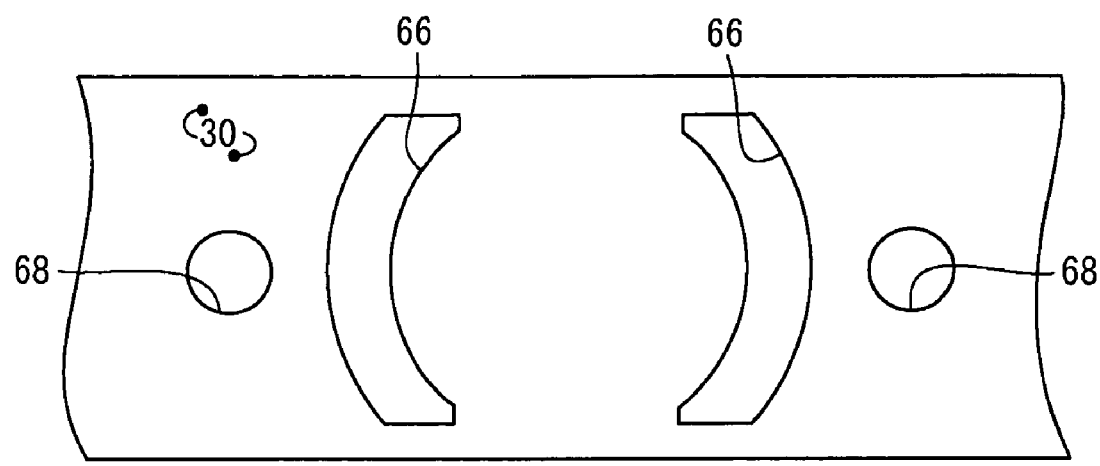
FIG. 5 Illustration depicting a placement surface.

As depicted in model form in FIG. 5, in the placement surface 30 there are formed through-holes 66, 66, provided as insertion holes, that pass through the surface in the thickness direction and have a shape generally approximating, but slightly larger than, the shape of the upper face of the main body support parts 56, 56; and through-holes 68, 68, provided as insertion holes, that pass through the surface in the thickness direction and have a shape generally approximating but slightly larger than the shape of the upper faces of the leg support parts 58, 58.

The carrying member 50 is attached to the lower side of the placement surface 30 of the stage 20. Specifically, the main body support parts 56 and the leg support parts 58 are passed through the through-holes 66, 68 respectively, from the back side of the placement surface 30. The main body support parts 56 and the leg support parts 58 are then passed through and pushed upwardly into the through-holes 66, 68. Since the main body support parts 56 and the leg support parts 58 have progressively larger dimension in top view towards the bottom, the carrying member 50 will become secured to the back side of the placement surface 30 by the recovery force of the through-holes 66, 68 and by frictional force between the mutual components. The extent of upward ramming of the main body support parts 56 and the leg support parts 58 will be limited by the positioning plate parts 52 coming into abutment against the back face of the placement surface 30. The carrying member 50 could also be furnished with a detaining mechanism such as catch hooks or the like.

Figure 6:
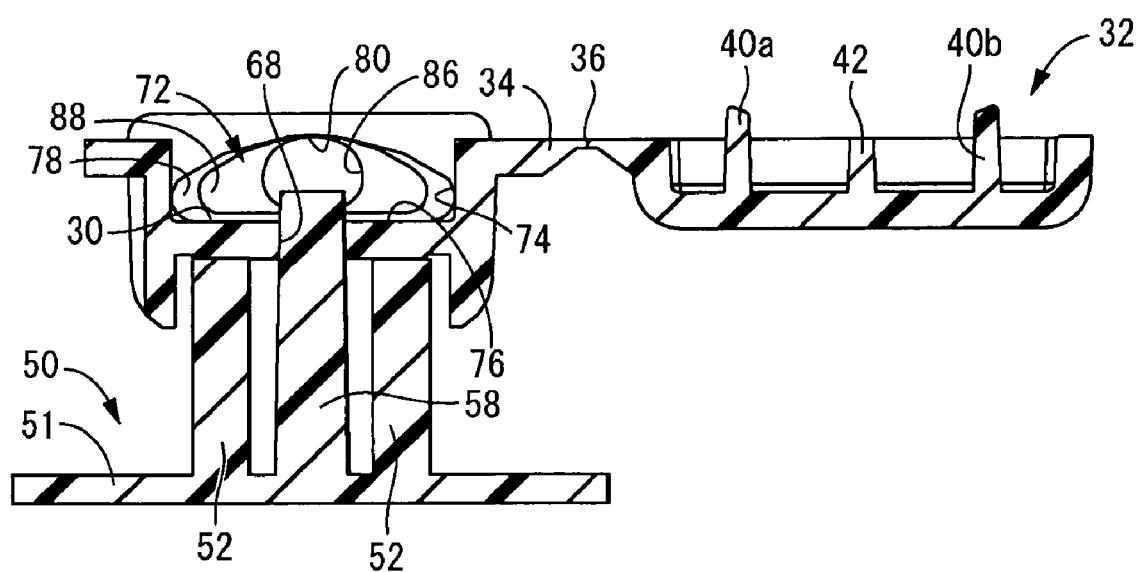
FIG. 6 Sectional illustration showing a model depiction of the 6-6 cross section in FIG. 1.

In this instance, as depicted in FIG. 6, the heightwise locations of the upper faces 61 of the main body support parts 56 and the upper end faces 64 of the leg support parts 58 will be situated at the location of maximum width dimension of an introduction part 78 provided as the base end of the insertion tube part to be described later (i.e. a location somewhat below the heightwise medial location of the introduction part 78).

Figure 7:
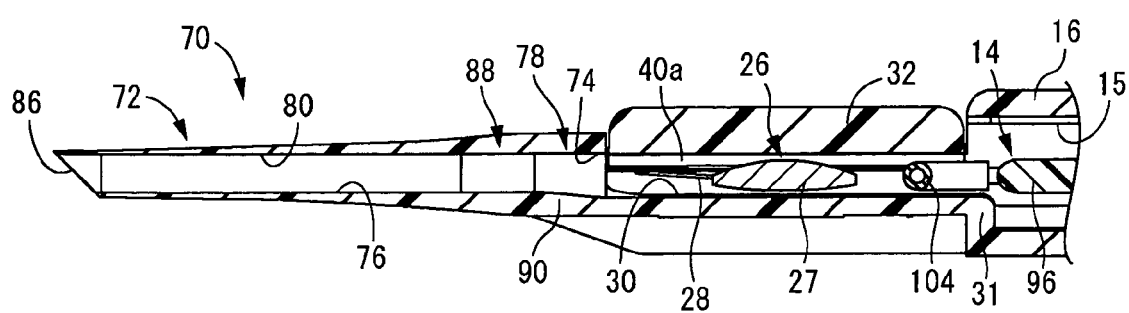
FIG. 7 Enlarged fragmentary sectional view of the insertion tool of FIG. 1.
Figure 8:
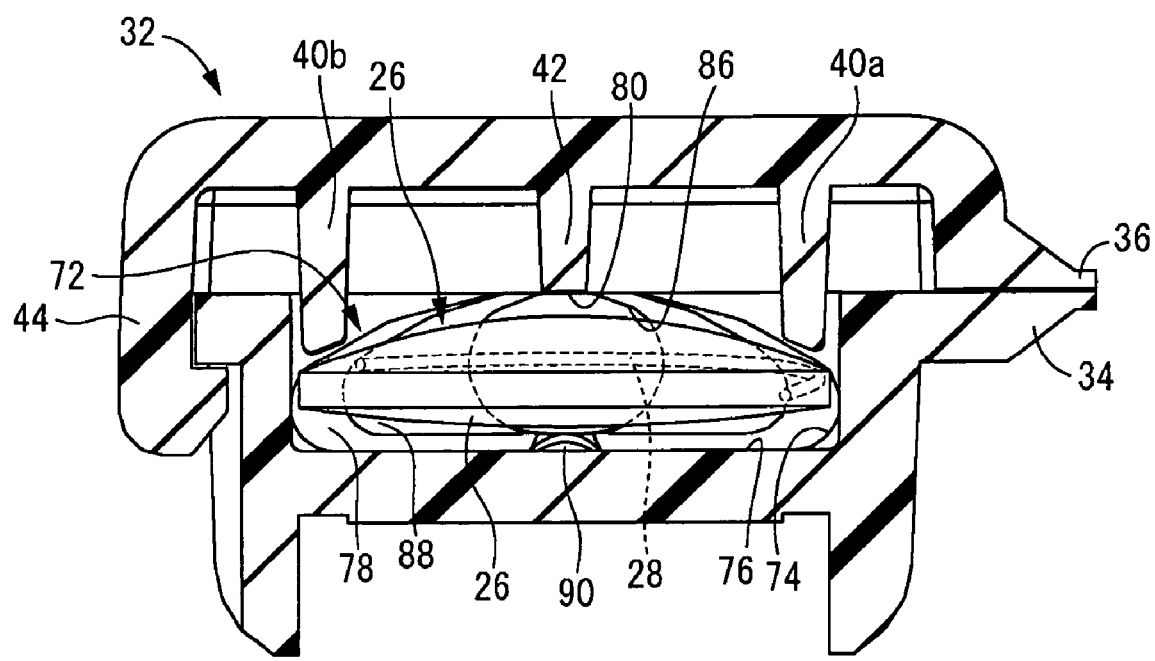
FIG. 8 Sectional illustration showing a model depiction of the 8-8 cross section in FIG. 1.

The intraocular lens 26 is placed on the upper faces 61, 61 of the main body support parts 56, 56 and the upper end faces 64, 64 of the leg support parts 58, 58 which project to the upward side of the placement surface 30. In this case, as depicted in FIG. 7, the intraocular lens 26 will be supported a prescribed distance away from the placement surface 30, and the lens in its entirety, inclusive of the optical region 25, will not come into contact with the placement surface 30. As noted earlier, because the intraocular lens 26 is supported exclusively at its retaining parts 28, 28 by the carrying member 50, the main body 27 never comes into contact with the carrying member 50 or the placement surface 30 with the lens carried on the carrying member 50. In FIGS. 7 and 8, the carrying member 50 has been omitted from the illustration in order to aid understanding.

Additionally, a nozzle part 70, provided as the insertion tube part, is integrally formed at the axial distal end of the tool body 12, to the front of the stage 20. The nozzle part 70 has progressive constricting outside contours going towards the distal end in the direction of extension from the base end on the tool body 12 side; and has a through-hole 72 that passes through its entire length in the direction of extension.

As depicted in FIG. 8, the through-hole 72 communicates with the stage 20 by connecting with the stage 20 at its base end aperture 74 that opens towards the stage 20 the tool body 12 side. In more detail, the base end aperture 74 as a whole has a flattened, generally elliptical shape whose base face 76 is defined by a flat face and whose upper face is generally arcuate in shape. The base face 76 connects steplessly to the placement surface 30 of the stage 20. The base end aperture 74 is formed so as to have maximum width dimension in a region slightly upward from the base face 76, with the maximum width dimension of the base end aperture 74 being approximately equal to the width dimension of the placement surface 30.

An introduction part 78 of progressively smaller cross sectional area going towards the distal end side from the base end aperture 74 is formed in the through-hole 72. In the introduction part 78, the width dimension of the base face 76 becomes progressively smaller towards the distal end, while the curvature of the lateral cross-sectional shape of both the left and right faces becomes progressively larger and the height dimension becomes smaller. The base face 76 of the introduction part 78 slopes gradually upward moving towards the distal end from the base end aperture 74. Meanwhile, the heightwise location of the upper face 80 of the through-hole 72 is generally unchanging. Thus, moving in the forward direction, in the introduction part 78 the base face 76 will come closer to the upper face 80, and the width dimension thereof will become progressively smaller.

Further, a constricted-diameter part 88 of progressively smaller cross sectional area towards the distal end aperture 86 is formed between the introduction part 78 and the distal end aperture 86 in the through-hole 72. In the constricted-diameter part 88, the lateral cross-sectional shape of both the left and right faces deforms to generally arcuate shape going towards the distal end, and the width dimensions of the upper face 80 and the base face 76 become progressively smaller. The heightwise distance separating the flat part of the upper face 80 and the flat part of the base face 76 in the constricted-diameter part 88, i.e. the height dimension of the constricted-diameter part 88, is generally unchanging. Thus, the distal end aperture 86 is of generally oval shape having flat parts on both its upper and lower faces, with the upper and lower faces connecting in generally elliptical shape.

An introduction projection 90 that projects slightly upward and extends linearly in the axial direction of the tool body 12 is formed in the widthwise center part of the base face 76 of the introduction part 78. This introduction projection 90 has a length dimension extending from the back end of the introduction part 78 to the back end of the constricted-diameter part 88. In the introduction projection 90, the base face 76 of the introduction part 78 is progressively higher going axially forward, thereby reaching a heightwise position equal to that of the base face 76 at the back end of the constricted-diameter part 88.

The tool body 12 of the present embodiment described above includes the integrally formed main tube part 16, stage 20, cover part 32, and nozzle part 70, and is constituted as a single component. Since the tool body 12 is made of a component that is light-transmissive, even with the stage 20 covered by the cover part 32, the intraocular lens 26 enclosed inside the tool body 12 will be visible through the cover part 32.

Figure 9:
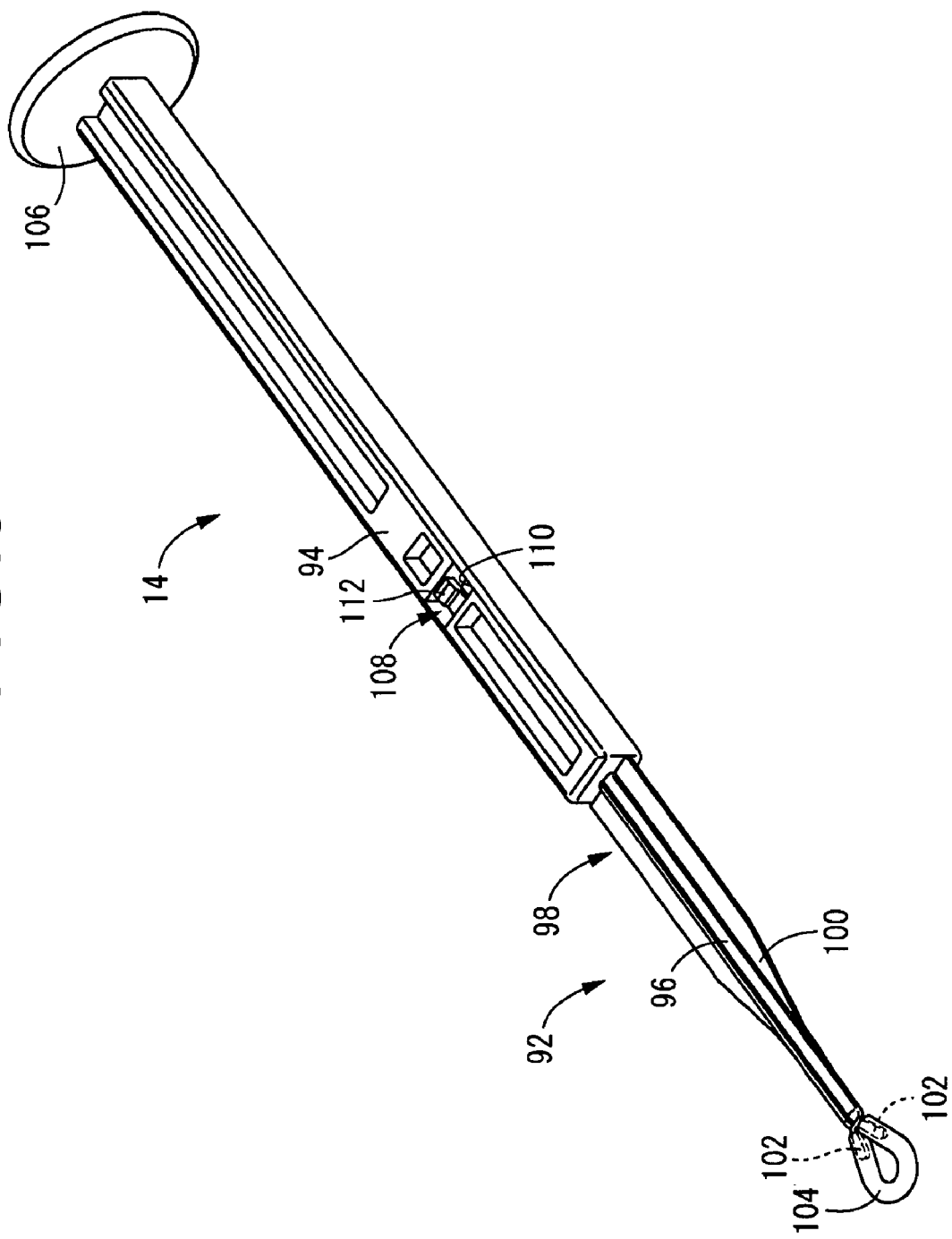
FIG. 9 Perspective view depicting a plunging member used in the insertion tool.

The plunger 14 provided as the plunger member is inserted from the back of the tool body 12 having the above structure, and is inserted through the through-hole 15. The plunger 14 is depicted in FIG. 9. The plunger 14 is a generally rod shaped member having an axial length dimension somewhat larger than the axial length dimension of the tool body 12; it includes an integrally formed working part 92 of generally flattened shape and a pass-through part 94 of generally oblong rod shape.

The working part 92 includes a rod-shaped part 96 extending along the center axis of the plunger 14; and flattened parts 98 of thin plate form extending to either side in the width direction from the rod-shaped part 96. The flattened parts 98 extend from the base end of the rod-shaped part 96 in the direction of the distal end with a width dimension approximately equal to that of the pass-through part 94; and starting at the approximately medial section in the lengthwise direction of the rod-shaped part 96 have pointed parts 100 of progressively smaller width dimension going towards a region somewhat rearward from the distal end part of the rod-shaped part 96. In this case, seen in top view the pointed parts 100 have contours so as to conform to the horizontal cross sectional shape of the introduction part 78 and the constricted-diameter part 88 in the nozzle part 70.

At the distal end edge of the rod-shaped part 96 there are integrally formed a pair of branched parts 102, 102 that branch in a generally "Y" shape towards the distal end direction. A tube 104 of hollow, round tube shape made of readily deformable elastic material, such as rubber for example, has been bowed in a generally loop-shaped configuration and its two ends attached slipped about the outside of the branched parts 102, 102. The tube 104 is thereby attached to the distal end edge of the plunger 14 in a generally loop-shaped configuration in top view. Since only the two ends of the tube 104 are slipped about the outside of the branched parts 102, 102, its lengthwise medial section situated at the distal end of the plunger 14 is readily deformable. In the present embodiment, the tube 104 constituted the deforming member.

Meanwhile, the pass-through part 94 has a length dimension that is slightly larger than the length dimension of the through-hole 15. The pass-through part 94 in substantially the entirety thereof has a generally "H" shaped transverse section whose width and height dimensions are slightly smaller than the width and height dimensions of the through-hole 15. A pushing plate part 106 of circular disk shape spreading out in the axis-perpendicular direction is formed at the back end edge of the pass-through part 94.

Additionally, a catch hook part 108 provided as retaining means is formed on the pass-through part 94. The catch hook part 108 is generally plate-shaped and projects into a through-hole 110 that passes in the axis-perpendicular direction through the pass-through part 94, and at its distal end part which projects into the through-hole 110 there is formed a catch projection 112 that projects to the outer side of the pass-through part 94 (in the present embodiment, upward). With the plunger 14 passed through the main tube part 16, the catch projection 112 will become engaged in a catch hole 114 that passes in the thickness direction through the main tube part 16, thereby positioning the plunger 14 relative to the main tube part 16. The formation locations of the catch projection 112 and the catch hole 114 will be established such that in their engaged state, the distal end section of the tube 104 projects slightly out from the through-hole 15 at a location a short distance into the stage 20 (the location depicted in FIG. 1). In the present embodiment, the catch projection 112 and the catch hole 114 are situated on the upper face of the insertion tool 10, but they could instead be situated on the lower face or a side face, for example.

In the intraocular lens insertion tool 10 having the above construction, first, with the distal end section of the plunger 14 inserted from the rear into the tool body 12 and positioned at the initial location (the location shown in FIG. 1 mentioned previously), the carrying member 50 will be attached from below the stage 20 to the tool body 12 as described previously. The main body support parts 56, 56 and the leg support parts 58, 58 of the carrying member 50 will thereby be positioned to the upper side of placement surface 30. Also, the intraocular lens 26 will be positioned resting on the upper faces 61, 61 of the main body support parts 56, 56 and the upper end faces 64, 64 of the leg support parts 58, 58.

Then, by bending the bending part 36, the aperture 29 of the stage 20 will be covered with the cover part 32 so that the intraocular lens 26 is set enclosed inside the tool body 12. The cover part 32 will be held in the closed state through engagement of the catch piece 44 in the catch notch 48.

By placing the cover part 32 in the closed state, the left and right guide plate parts 40*a*, 40*b* and the center guide plate part 42 will be disposed projecting out towards the placement surface 30. In this instance, as depicted in FIG. 8, the heightwise locations of the projecting distal ends of the left and right guide plate parts 40*a*, 40*b* will be approximately equivalent to the heightwise location of the left and right sections of the upper face 80 in the base end aperture 74 as seen in an axial projection of the tool body 12. Additionally, the heightwise location of the projecting distal end of the center guide plate part 42 will be approximately equivalent to the heightwise location of the upper face 80 of the base end aperture 74 as seen in an axial projection of the tool body 12. The projecting distal ends of the left and right guide plate parts 40*a*, 40*b* are sloped along the base end aperture 74 as seen in an axial projection of the tool body 12. This serves to limit excessive up and down movement of the intraocular lens 26 enclosed inside the tool body 12. The plunger 14 may be inserted into the tool body 12 after the intraocular lens 26 has been placed on the carrying member 50, or after the cover part 32 has been closed.

The intraocular lens 26 is enclosed within the insertion tool 10 in the manner described above. In this embodiment, the insertion tool 10 with the intraocular lens 26 accommodated therein will then be subjected to a sterilization process etc., then packaged and shipped.

When the intraocular lens 26 is to be inserted into the eye using the insertion tool 10 according to the present embodiment, first, the carrying member 50 is pulled downward from the main tube part 16 to detach it from the main tube part 16. By so doing, the main body support parts 56, 56 and the leg support parts 58, 58 which were supporting the intraocular lens 26 will be withdrawn downwardly from above the placement surface 30 so that the intraocular lens 26 now rests on the placement surface 30. In the insertion tool 10 of the present embodiment, because the placement surface 30 is defined by a flat face, the intraocular lens 26 can be positioned resting stably thereon. Since the width dimension of the recessed slot 22 is approximately equal to the diameter dimension of the intraocular lens 26 when it is placed on the carrying member 50, rotation of the intraocular lens 26 in the circumferential direction while resting on the placement surface 30 will be prevented as well.

Next, with the distal end section of the nozzle part 70 inserted through a surgical incision made in the ocular tissue, the pushing plate part 106 of the plunger 14 will be pushed towards the tool body 12 side. By so doing, the tube 104 of the plunger 14 will come into contact against the retaining parts 28 of the intraocular lens 26 resting on the placement surface 30, guiding the intraocular lens 26 towards the base end aperture 74.

In preferred practice, prior to plunging of the intraocular lens 26, an appropriate lubricant will be injected into the stage 20 or nozzle part 70 if needed. In the present embodiment in particular, an injection hole 116 provided as a lubricant injection hole has been formed passing through the cover part 32 in the thickness direction so that the lubricant can be injected through the injection hole 116 with the cover part 32 closed. However, injection of lubricant could also be accomplished, for example, by injection through the base end aperture 74 of the nozzle part 70. By opening the cover part 32 and injecting lubricant from the aperture 29 of the stage 20; or by withdrawing the plunger 14 from the tool body 12 and injecting lubricant from the aperture at the back end of the through-hole 15. In this regard, in the present embodiment in particular, the readily deforming tube 104 has been provided to the distal end section of the plunger 14. Thus, pressure can be exerted effectively on the lubricant that has been injected into the stage 20, making it possible for the intraocular lens 26 to be pushed out by this pressure, while also effectively preventing damage to the delicate retaining parts 28, 28.

The intraocular lens 26 which has been guided from the base end aperture 74 into the introduction part 78 will then undergo bowing deformation such that its main body 27 becomes upwardly convex due to the widthwise center section of the main body 27 coming into contact with the introduction projection 90. The intraocular lens 26 positioned within the introduction part 78 thereby be imparted with initial deformation conforming to the shape of the through-hole 72, and be pushed into the constricted-diameter part 88.

By plunging the plunger 14 further along, the intraocular lens 26 will now be guided in the distal end direction through the constricted-diameter part 88 and become deformed to even smaller size, then pushed to the outside of the insertion tool 10 through the distal end aperture 86 and inserted into the eye. In the present embodiment, the extent to which the plunger 14 can be plunged into the tool body 12 will be limited through the distal end sections of the pointed parts 100 being detained by the through-hole 72, and at the location of maximum plunger stroke, the tube 104 will project slightly out from the distal end aperture 86.

In the insertion tool 10 constructed in the above manner, by placing the intraocular lens 26 on the carrying member 50, the intraocular lens 26 can be easily enclosed within the tool, and can be enclosed in a stable manner. Since the lens can be enclosed without deforming its main body 27 inclusive of the optical region 25, the risk of bowing deformation of the optical region 25 over time can be reduced, making it possible for the intraocular lens 26 to be enclosed within the insertion tool 10 for an extended period. This makes it possible for the intraocular lens 26 to be packaged and stored in a form enclosed within the insertion tool 10, and also eliminates the inconvenience entailed in enclosing the intraocular lens in the insertion tool at the time of surgery.

In the present embodiment in particular, with the lens carried on the carrying member 50, the main body 27 will be in a state of non-contact with other components such as the carrying member 50 and the placement surface 30, thus reducing the risk of damage to the main body 27. Moreover, due to the fact that the cover part 32 has been provided with the left and right guide plate parts 40*a*, 40*b* and the center guide plate part 42, excessive upward displacement of the intraocular lens 26 carried on the carrying member 50 will be restricted, making it possible to reduce the risk of the intraocular lens 26 coming off from the carrying member 50 due to vibration etc. during shipping, so that it is maintained enclosed in the insertion tool 10 in a stable manner.

Furthermore, during use of the insertion tool 10 according to the present embodiment, it is possible for the intraocular lens 26 to be placed on the placement surface 30 by a very simple operation, namely, of detaching the carrying member 50. Since the intraocular lens 26 is positioned thusly while the stage 20 is covered by the cover part 32, the risk of the intraocular lens 26 falling out is eliminated; and due to reduced contact of the intraocular lens 26 with the outside environment, hygienic advantages are afforded as well.

Additionally, in the insertion tool 10 of the present embodiment, because upward displacement of the intraocular lens 26 will be restricted by the left and right guide plate parts 40*a*, 40*b* and the center guide plate part 42 as the intraocular lens 26 is pushed along, the intraocular lens 26 can be guided stably into the base end aperture 74, reducing the risk of damage to the intraocular lens 26 caused by it becoming caught, etc. As the intraocular lens 26 which has been guided from the base end aperture 74 into the introduction part 78 comes into contact against the introduction projection 90, the intraocular lens 26 can be imparted with consistent initial deformation, making it possible stable deformation of the intraocular lens 26 to take place in the nozzle part 70.

In addition, in the insertion tool 10 of the present embodiment, as the distal end of the plunger 14 is readily deformable due to the provided tube 104, it will be possible to avoid subjecting the intraocular lens 26 to unnecessary force as the intraocular lens 26 is pushed along, reducing the risk of damage or breakage of the intraocular lens 26 as it is pushed along. Further, in the present embodiment in particular, because the tube 104 has a generally loop configuration, it will be possible for it to advantageously conform to the change in cross-sectional shape from the horizontally long cross section of the stage 20 to the generally oblong cross section of the nozzle part 70.

The distal end shape of the plunger 14 of the present embodiment will more effectively exhibit its advantages if a lubricant is injected into the stage 20 and the nozzle part 70. Specifically, as the tube 104 has been given a readily deformable, generally loop shape, the pressure exerted on the lubricant can be used to push along the intraocular lens 26 so as to more effectively avoid damage to the delicate retaining parts 28. Furthermore, since the plunger 14 can effectively conform to the change in cross-sectional shape of the region from the stage 20 to the nozzle part 70, pressure can be more effectively exerted on the lubricant, and the intraocular lens 26 can be pushed in a more stable manner.

While the invention has been described detail hereinabove in terms of a preferred embodiment, this is merely exemplary and the invention should not be construed as limited in any way to the specific disclosure of the embodiment above. Components and parts that are substantially identical to those in the preceding embodiment have been assigned the same symbols as in the preceding embodiment and will not be discussed in any detail.

Figure 10:
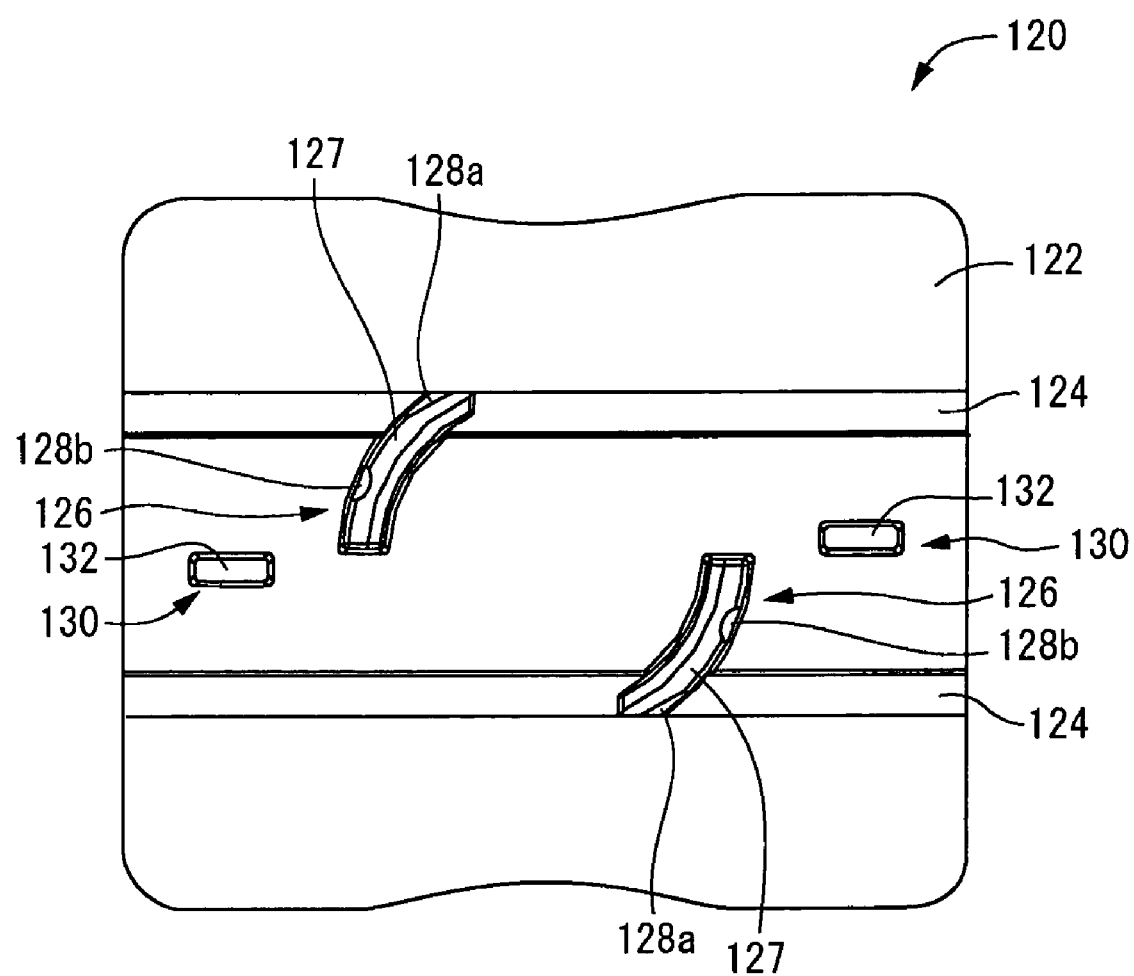
FIG. 10 Top view depicting a different embodiment of the carrying member.

For example, the specific shapes of the carrying member and the carrying parts are not limited to ones similar to the shapes discussed above. FIG. 10 depicts a carrying member 120 according to a different embodiment of the carrying member. The carrying member 120 is generally similar to the carrying member 50 described above in that a plate part 122 of generally oblong plate shape is provided with a pair of mating plate parts 124, 124 integrally formed thereon and that project upward and extend approximately parallel across the entire length of the plate part 122 in the longitudinal direction.

On the carrying member 120 there are formed main body support parts 126, 126 provided as support parts that extend respectively from each of the mating plate parts 124, 124 towards the opposed respective mating plate part 124, 124, and whose contours in top view is of arcuate shape equivalent to approximately one-fourth the circumference. Additionally, an upwardly projecting outside projecting piece 128a is formed to the circumferential outside edge side of the upper face 127 constituting the projecting distal end face of each main body support part 126. An upwardly projecting inside projecting piece 128b is formed spaced a prescribed distance circumferentially inward from the outside projecting piece 128a.

To the outside of the main body support parts 126, 126 there are formed leg support parts 130, 130 that are provided as a pair of leg support parts projecting upward from the plate part 122. In the present embodiment, the leg support parts 130 are situated somewhat to the outside of the main body support parts 126 in the axial direction of the mating plate parts 124, with respect to the opposed projecting distal ends of the main body support parts 126 that lead to the mating plate parts 124. The pair of leg support parts 130, 130 are formed at slightly different locations in the direction of extension of the mating plate parts 124. The contours of the upper end face 132 constituting the projecting distal end face of the leg support parts 130 in the present embodiment are generally oblong in shape and extend in approximately the same direction as the direction of extension of the mating plate parts 124.

Like the carrying member 50 discussed previously, the carrying member 120 constructed in the above manner is adapted to be attached to the back side of the placement surface 30. Specifically, while not depicted in the drawing, the placement surface 30 is perforated by through-holes of shape corresponding to the contours of the upper faces of the main body support parts 126, 126 and the formed leg support parts 130, 130 in the present embodiment. The main body support parts 126 and the leg support parts 130 progressively become slightly larger in size towards the bottom. Thus, the carrying member 120 is adapted to be secured to the back side of the placement surface 30 by pushing the main body support parts 126 and the formed leg support parts 130 into the through-holes which have been formed in the placement surface 30.

During placement of the intraocular lens 26 on the carrying member 120, the base ends 60 of the retaining parts 28 will be positioned resting on the upper faces 127 of the main body support parts 126, while the outwardly extending parts of the retaining parts 28 will be positioned extending to the outside of the main body support parts 126 from between the opposing faces of the outside projecting piece 128a and the inside projecting piece 128b so as to be positioned resting on the upper end faces 132 of the leg support parts 130. Thus, as in the embodiment described previously, the intraocular lens 26 can be prevented from rotating in the circumferential direction, while its main body 27 can be positioned in a non-contacting state. According to the present embodiment, the area of contact between the intraocular lens 26 and the carrying member 120 can be smaller, thereby further reducing the risk of damage to the lens due to contact with other components.

The leg support parts 58, 130 of the carrying members 50, 120 discussed above are each disposed in partial contact with the retaining parts 28 so that the risk of damage caused by contact may be reduced owing to the small contact area with one another. However, the leg support parts are not limited to such shapes, and could instead be formed so as to extend along the contours of the retaining parts 28 and support the retaining parts 28 substantially in their entirety.

Figure 11:
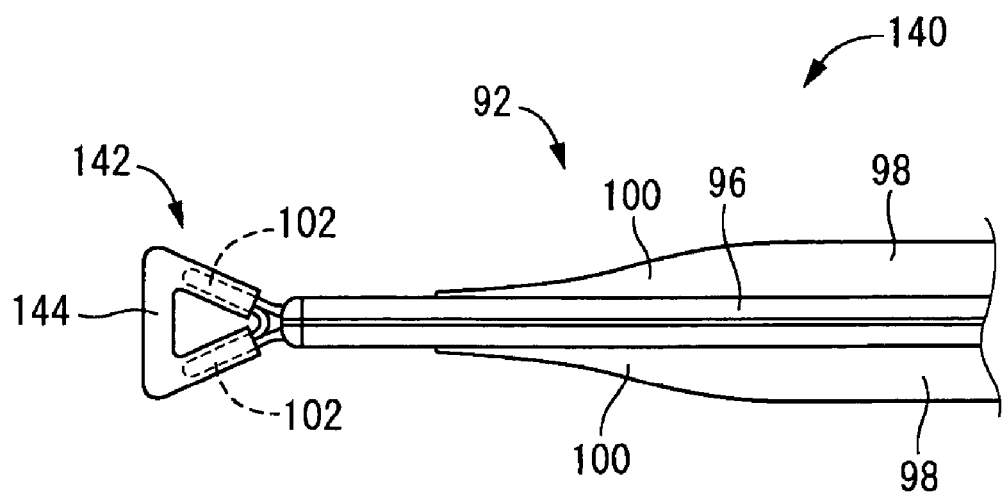
FIG. 11 Top view depicting a different embodiment of the plunging member.

The specific shape of the plunging member is not limited to the shape described above. A number of plunging members suitable for use in the present invention are described below by way of example. For example, FIG. 11 depicts in top view the distal end section of a plunger 140 according to a different embodiment of the plunging member. This plunger 140 differs in terms of the specific shape of the tube 104 of the plunger 14 described previously. The tube 142 provided as the deforming member of the plunger 140 is of hollow, round tube shape made of readily deformable elastic material such as rubber for example, and has been bent at two locations along its length to produce a generally triangular shape in top view. The two ends of the tube 142 are attached slipped about the outside of the branched parts 102, 102. The two branched parts 102, 102 and the tube 142 thereby give the distal end section of the plunger 140 a triangular shape in top view, with the tube 142 constituting a linear part 144 situated at the distal end edge of the plunger 140 and extending in a straight line in the direction perpendicular to the axis of the tool body 12. The width dimension of this linear part 144 will be approximately equal to the width dimension of the recessed slot 22.

According to this arrangement, the linear part 144, i.e. the distal end edge of the plunger 140, can be disposed spanning substantially the entire width of the recessed slot 22. Thus, particularly in instances where the interior of the recessed slot 22 is to be filled with a lubricant or the like, it will be possible to impart generally uniform pressure in the plunging direction across substantially the entire width of the recessed slot 22 so that plunging of the intraocular lens 26 can take place in a more stable manner. Also, as with the plunger 14 discussed previously, since the linear part 144 is readily deformable, the intraocular lens 26 will not be subjected to unnecessary force.

Figure 12:
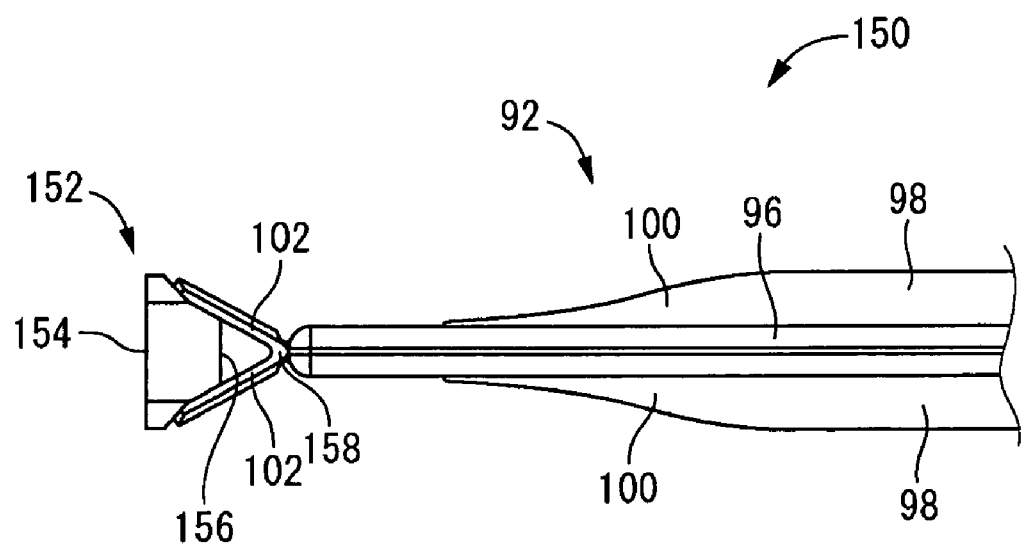
FIG. 12 Top view depicting yet another different embodiment of the plunging member.

FIG. 12 depicts in top view the distal end section of a plunger 150 according to yet a different embodiment of the plunging member. The distal end section of the plunger 150 is provided with a working member 152 as the deforming member. The working member 152 has a width dimension at its front end edge 154 that is approximately equal to the width dimension of the recessed slot 22, while its width dimension at its back end edge 156 is approximately equal to the distance separating the branched parts 102, 102 at a medial location in the axial direction of the plunger 150. Through this arrangement, the working member 152 will be situated in the distal end section of the plunger 150 in such a way that its side edges in proximity to its back end edge 156 are clasped between the branched parts 102, 102. The working member 152 may be fixedly secured to the branched parts 102, 102 with adhesive or the like; or not fixedly attached. In this instance, the front end edge 154 of the working member 152 will project out somewhat from the front edge sections of the branched parts 102, 102. There is an appropriate gap between the back end edge 156 and the base end 158 of the branched parts 102, 102. The working member 152 is made of easily deformable material having elasticity, such as rubber or silicone. In this embodiment, substantially uniform pushing force can be exerted in stable manner across the entire width of the recessed slot 22.

Figure 13:
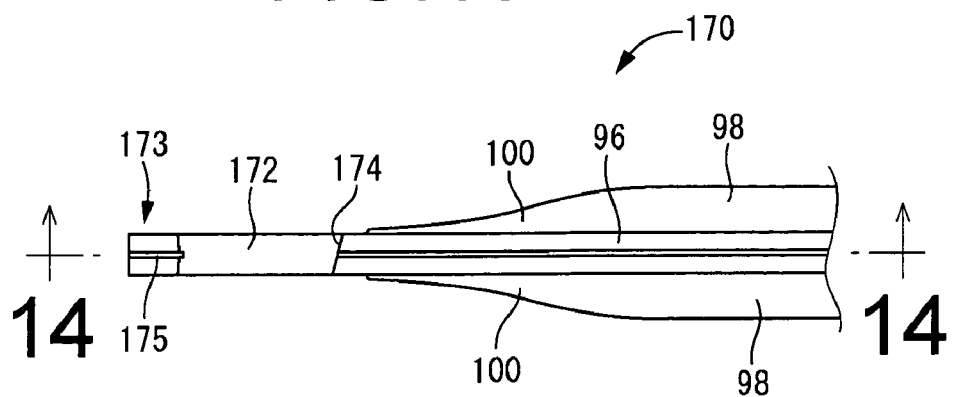
FIG. 13 Top view depicting yet another different embodiment of the plunging member.
Figure 14:
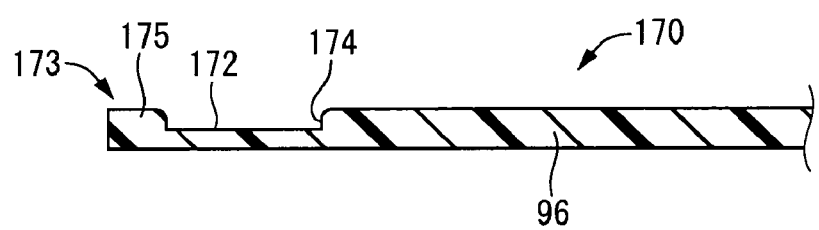
FIG. 14 Sectional view showing the 14-14 cross section in FIG. 13.

FIGS. 13 and 14 depict in top view and in cross sectional view the distal end of a plunger 170 according to yet a different embodiment of the plunging member. The plunger 170 according to this embodiment has a notch 172 that opens upward, formed at the distal end of a rod-shaped part 96. The rod-shaped part 96 is of generally rod shape extending in a straight line with generally circular cross section. The notch 172 is formed across the entire width of the rod-shaped part 96, and spans a prescribed dimension in the axial direction starting from a location somewhat rearward in the axial direction from the distal end edge 173 of the rod-shaped part 96. By so doing, the distal end of the rod-shaped part 96 will have an axial cross section that is a generally right-angle three-sided polygon, with the region where the notch 172 is formed having generally semicircular shape in cross section in the axis-perpendicular direction. In the present embodiment in particular, the back wall part 174 of the notch 172 that constitutes its axial rearward end edge is somewhat inclined with respect to the axis-perpendicular direction of the rod-shaped part 96, with the slope of this back wall part 174 being approximately equal to the slope of the outside peripheral edge of the intraocular lens 26 situated in opposition to it in the axial direction. The axial dimension of the notch 172 will be larger than the width dimension of at least the extending sections of the retaining parts 28 of the intraocular lens 26. An upward projecting part 175 that projects upward and extends in the axial direction widthwise medial section of the rod-shaped part 96 is formed in the widthwise medial section of the rod-shaped part 96.

With the plunger 170 constructed as described above, during plunging of the intraocular lens 26, with the retaining parts 28 positioned in the notch 172 the distal end edge 173 of the plunger 170 will be placed in contact with the peripheral edge of the main body 27. By so doing, it will be possible to avoid damage to the delicate retaining parts 28 due to the plunging force of the plunger 170 being exerted on the retaining parts 28. The plunging force of the plunger 170 can be directed onto the main body 27 so that the intraocular lens 26 can be plunged in a stable manner. Furthermore, even where the intraocular lens 26 has been guided into the through-hole 72, since a prescribed gap will form between the notch 172 and the inside peripheral face (upper face 80) of the through-hole 72 and the retaining parts 28 will be positioned within this gap, the risk of damage due to the retaining parts 28 becoming pinched between the plunger 170 and the inside peripheral face of the through-hole 72 can be effectively reduced. Moreover, in the present embodiment in particular, because the slope of the back wall part 174 is approximately equal to the slope of the retaining parts 28, even if the retaining parts 28 should come into contact against the back wall part 174, the retaining parts 28 will be subjected to working force directed towards the main body 27 in a manner similar to when the lens has been placed in the eye, thereby reducing the risk of deformation and possible damage to the retaining parts 28 by force directed in unwanted directions.

Figure 15:
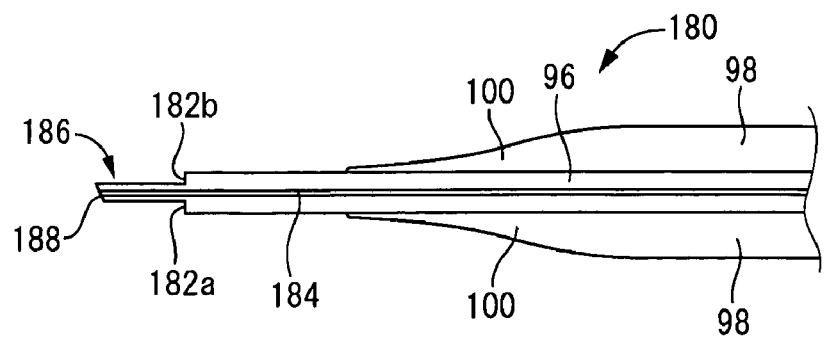
FIG. 15 Top view depicting yet another different embodiment of the plunging member.

FIG. 15 depicts in top view the distal end of a plunger 180 according to yet a different embodiment of the plunging member. The plunger 180 of the present embodiment is provided with notches 182a, 182b of prescribed dimension in the axial direction at both widthwise ends of the distal end edge of the rod-shaped part 96. In the present embodiment, the rod-shaped part 96 is generally rod shaped and extends in a straight line with generally unchanging, generally oval shape having linear parts 184 at the top and bottom ends. At the widthwise ends of the rod-shaped part 96 notched zones of prescribed dimensions have been made to the rear in the axial direction from the distal end edge, thereby defining the notches 182a, 182b at both widthwise ends of the rod-shaped part 96, as well as defining a working part 186 between the notches 182a, 182b. The dimensions of the notches 182a, 182b in the axis-perpendicular direction are equal to approximately one-fourth the width dimension of the rod-shaped part 96. In the present embodiment in particular, the distal end edge 188 of the working part 186 slopes at an incline approximately equal to the incline of the outside peripheral edge of the axially facing base end 60 of the retaining part 28, seen in top view.

With the plunger 180 constructed as described above, during plunging of the intraocular lens 26 this distal end edge 188 will be disposed in contact with the outside peripheral edge of a base end 60 of the intraocular lens 26. As the plunger 180 is plunged further inward, the intraocular lens 26 will become deformed to upwardly convex shape by the introduction projection 90 and be pushed into the through-hole 72. The retaining part 28 situated on the plunger 180 side will thereby experience deformation along the inside peripheral face of the through-hole 72 as well. In this instance, in the plunger 180 of the present embodiment, gaps are defined between the inside peripheral face of the through-hole 72 and the notches 182a, 182b; and the base ends 60 of the retaining parts 28, as well as the extending sections thereof in proximity to the base ends 60, will be positioned within these gaps. The risk of damage to the retaining parts 28 due to becoming pinched between the plunger 180 and the inside peripheral face of the through-hole 72 can be reduced thereby. In the present embodiment in particular, because the distal end edge 188 slopes along the contour of the outside peripheral edge of the base end 60, point contact of the distal end edge 188 against the base end 60 can be largely avoided, thereby reducing the risk of damage to the retaining part 28.

The specific shape of the guide projections provided on the covering part is not limited to the shape described above. For example, in the preceding embodiment, a single center guide plate part 42 extends over the widthwise center of the cover part 32, and a pair of left and right guide plate parts 40a, 40b are formed to either side thereof. However, it would be possible for example to instead form, in place of the center guide plate part 42, a pair of guide plate parts to either side of the widthwise center of the cover part 32 so as to provide a total of four guide plate parts including the left and right guide plate parts 40a, 40b.

In the embodiment described above, the introduction projection 90 is defined as a single band in the widthwise center of the base face 76 of the introduction part 78, but the number of introduction projections is not limited to one, and several introduction projections could be provided.

Figure 16:
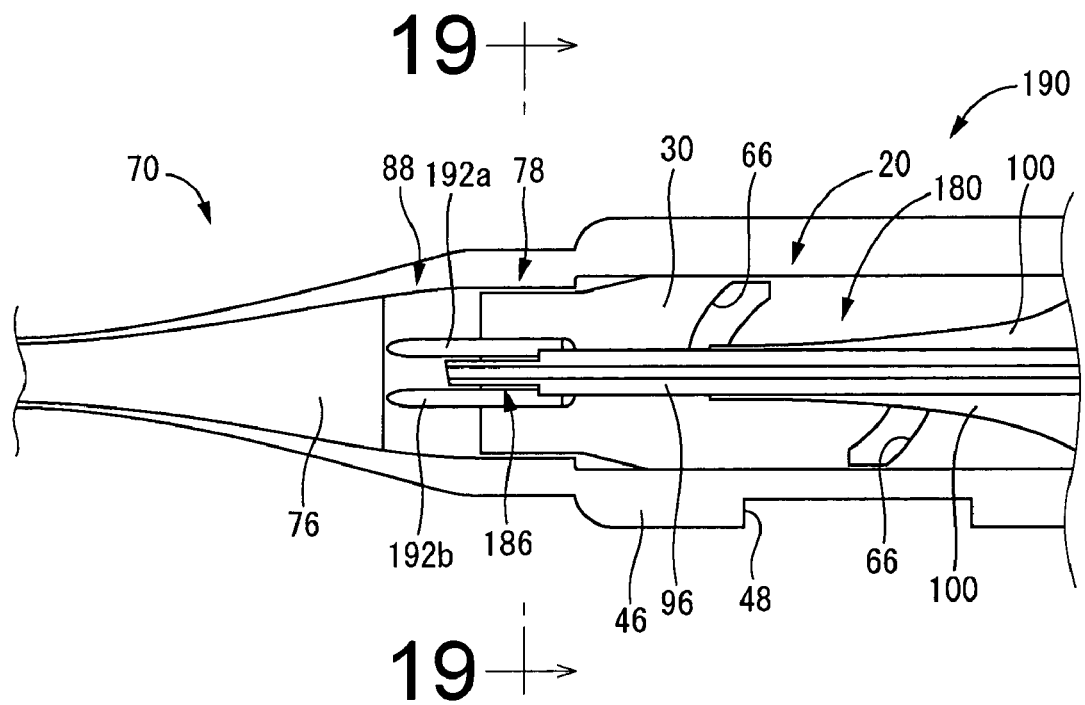
FIG. 16 Top view depicting a different embodiment of an tool body.
Figure 17:
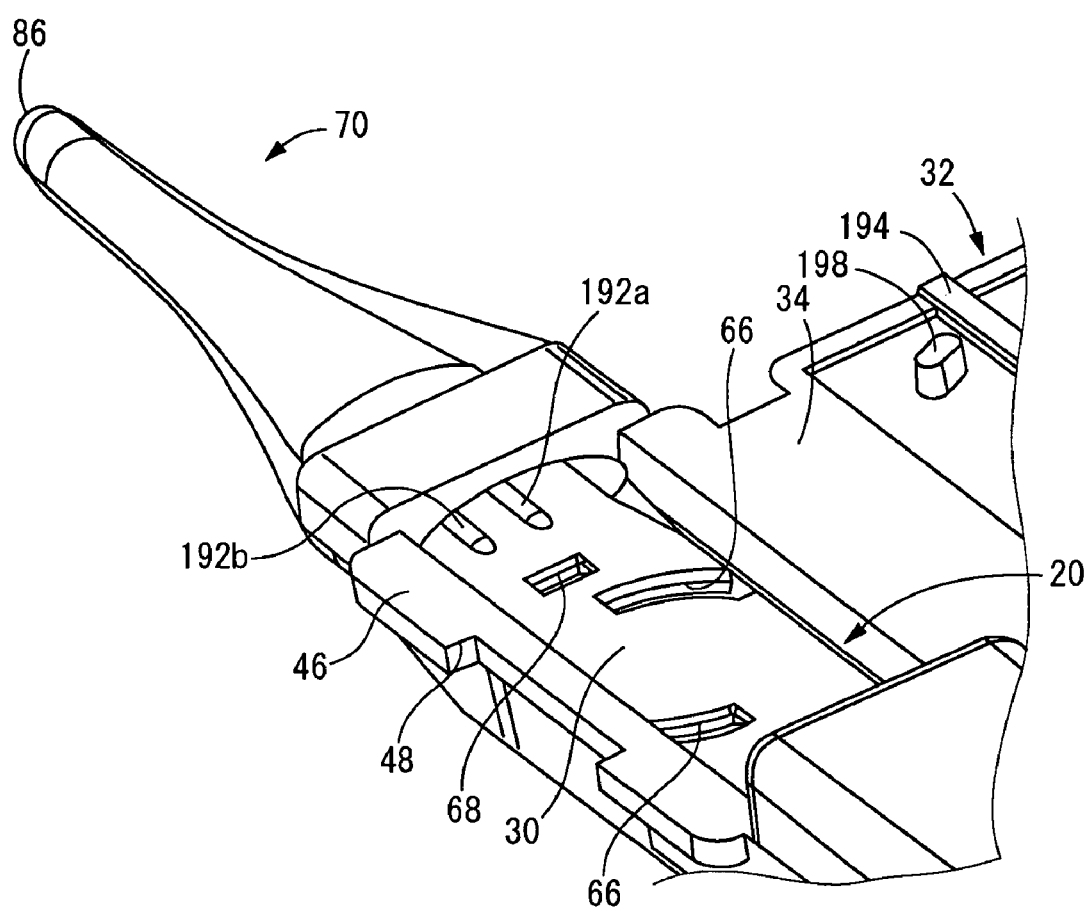
FIG. 17 Perspective view depicting the tool body.
Figure 18:
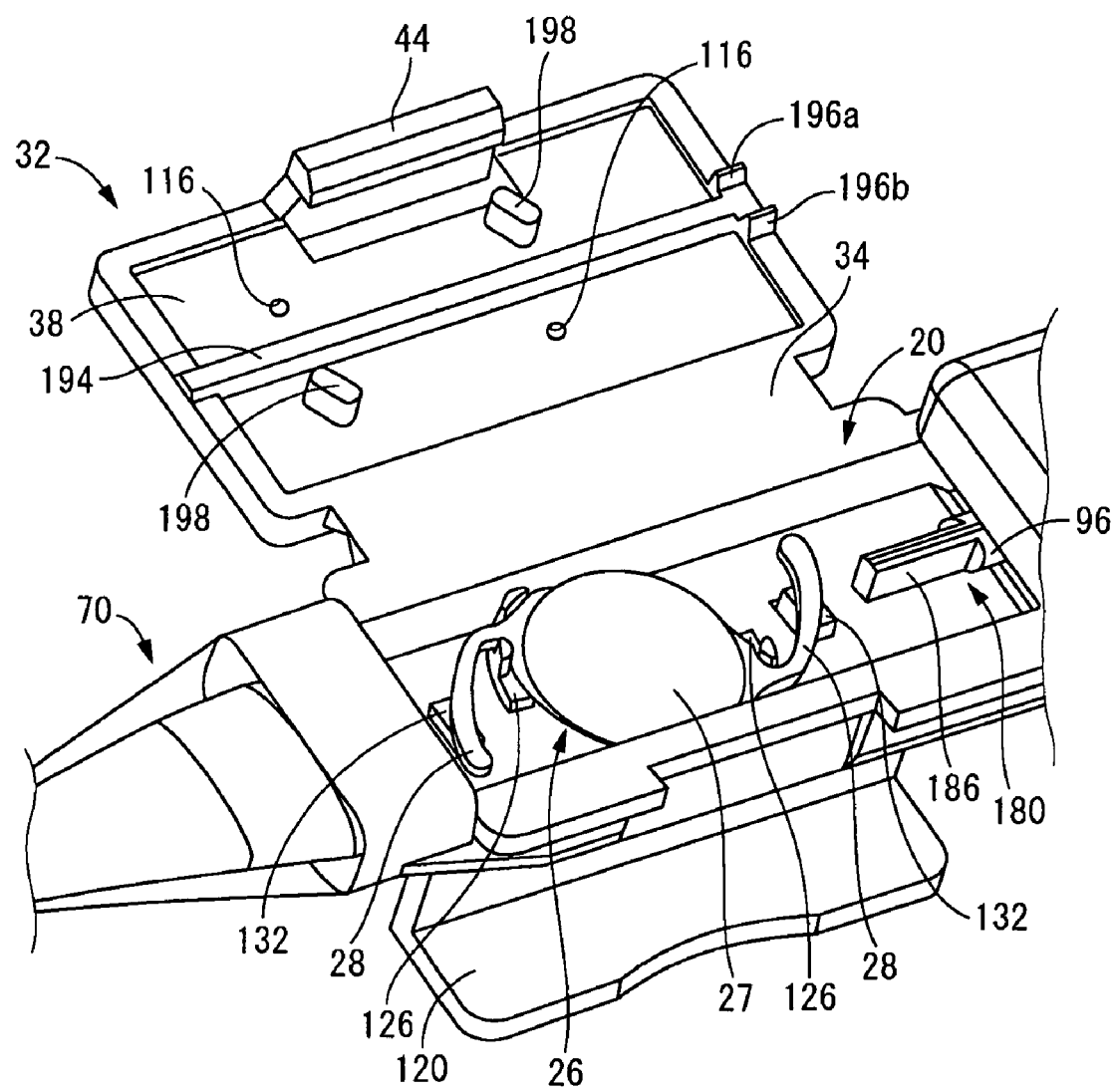
FIG. 18 Perspective view depicting the tool body.
Figure 19:
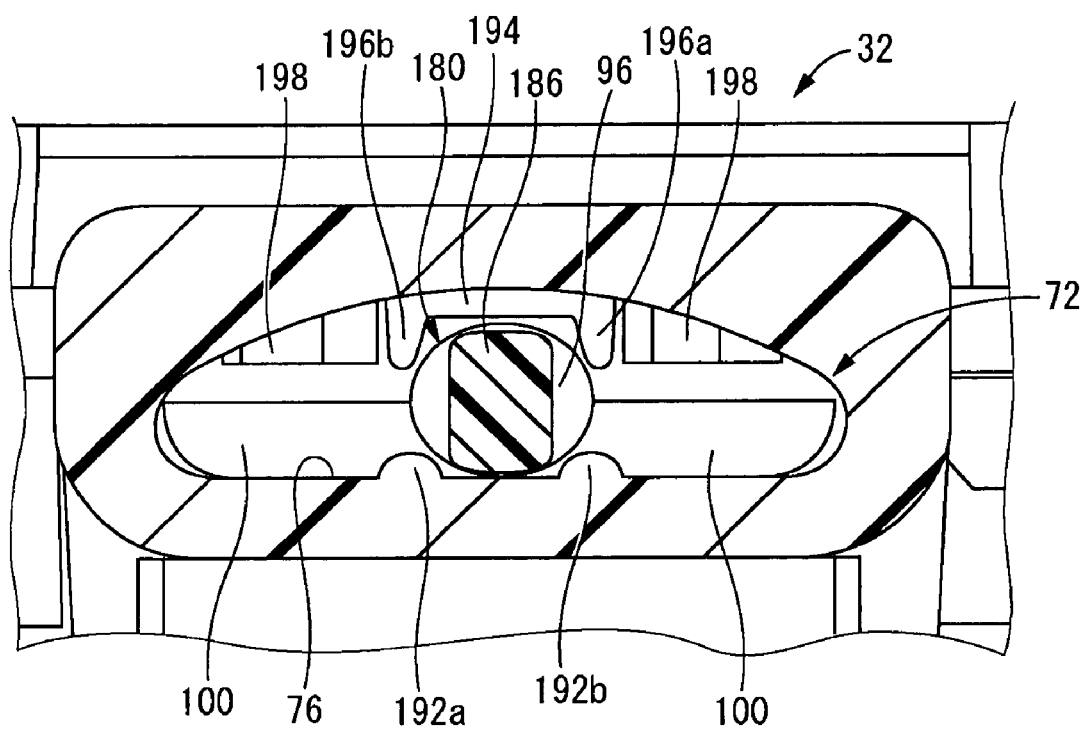
FIG. 19 Sectional illustration showing a model depiction of the 19-19 cross section in FIG. 16.

As an example of such an tool body provided with a plurality of introduction projections, an tool body 190 according to another embodiment is depicted in FIGS. 16 to 19. The tool body 190 has a shape generally identical to that of the tool body 12 described earlier, but differs from the preceding tool body 12 in that a pair of introduction projections 192a, 192b have been formed in the widthwise center section of the base face 76 of the introduction part 78. In FIG. 16 and FIG. 19, the aforementioned plunger 180 provided as the plunging member is shown inserted into the tool body 190. However, no particular limitation is imposed as to the specific shape of the plunging member, and it would be possible to instead employ inter alia any of the plungers 14, 140, 150, 170 taught in the preceding embodiments for example. In FIGS. 16, 17, and 19, the intraocular lens 26 has been omitted from the illustration, and the carrying member 120 is shown detached. In FIG. 16, the cover part 32 has been omitted from the illustration.

The introduction projections 192a, 192b of the tool body 190 respectively project upward a slight distance from the base face 76 in the introduction part 78, and extend in a straight line in the axial direction of the tool body 190. The dimension of these introduction projections 192a, 192b in the axial direction, i.e. their lengthwise dimension, extends from the back end of the introduction part 78 to the front end of the constricted-diameter part 88. As the base face 76 become progressively taller moving forward in the axial direction in the constricted-diameter part 88, at the front end of the constricted-diameter part 88, the introduction projections 192a, 192b will be situated at the same heightwise location as the base face 76.

These introduction projections 192a, 192b are disposed to either side of the widthwise center of the base face 76, so as to be generally parallel and spaced apart from one another by a prescribed distance in the axis-perpendicular direction of the tool body 190. The distance separating the introduction projections 192a, 192b will preferably be a dimension slightly larger than the width dimension of the distal end of the plunging member. In the present embodiment in particular, as depicted in model form in FIG. 19, the distance separating them will be somewhat larger than the width dimension of the working part 186 of the plunger 180 so that small gaps are present between the rod-shaped part 96 and the introduction projections 192a, 192b.

In the present embodiment in particular, as depicted in FIG. 18, a center guide projecting part 194 that extends in the axial direction of the tool body 190 has been integrally formed at the widthwise center of the opposed face 38 of the cover part 32. The projecting dimension of the center guide projecting part 194 is somewhat greater than the projecting dimension of the thick outside peripheral edge part that extends about the entire perimeter of the opposed face 38. It has a beam configuration that extends in a straight line across the entire length of the cover part 32.

A pair of left and right guide projecting parts 196a, 196b are formed to the back end side of the cover part 32 at the connecting region between the center guide projecting part 194 and the outside peripheral edge of the opposed face 38. The left and right guide projecting parts 196a, 196b are integrally formed with the cover part 32 and project out from the thick outside peripheral edge part of the opposed face 38. The distance separating their opposing faces is slightly smaller than the diameter dimension of the rod-shaped part 96 of the plunger 180. In the present embodiment in particular, the left and right guide projecting parts 196a, 196b have generally triangular cross section and are rounded at their projecting distal end.

In the present embodiment in particular, a pair of injection holes 116, 116 and a pair of contact projecting parts 198, 198 have been formed on the cover part 32 to either side of the center guide projecting part 194, and are respectively situated in opposition diagonally across the cover part 32. The contact projecting parts 198, 198 are integrally formed with the cover part 32 and project out from the opposed face 38. The heightwise location of their projecting distal ends approximately coincides with that of the projecting distal ends of the left and right guide projecting parts 196a, 196b. With the cover part 32 closed, the contact projecting parts 198, 198 will be respectively positioned above the retaining parts 28, 28 of the intraocular lens 26 supported on the carrying member 120, and function to limit excessive upward displacement of the intraocular lens 26 through contact with the intraocular lens 26 when it undergoes upward displacement.

When the cover part 32 in the tool body 190 constructed in the above manner is closed, the center guide projecting part 194 and the left and right guide projecting parts 196a, 196b will be positioned above the plunger 180 as depicted in FIG. 19. In this instance, the distance separating the center guide projecting part 194 and the placement surface 30 will be slightly larger than the diameter dimension of the rod-shaped part 96 of the plunger 180, thereby limiting displacement of the plunger 180 in the vertical direction. Additionally, because the left and right guide projecting parts 196a, 196b are positioned to the left and right sides above the rod-shaped part 96 with the rod-shaped part 96 between them, displacement of the plunger 180 in the left-right direction will be limited as well. Thus, during plunging of the plunger 180, excessive displacement of the plunger 180 in the diagonal direction will be limited by the center guide projecting part 194 and the left and right guide projecting parts 196a, 196b so that the plunger 180 can be plunged in a stable manner in the axial direction. In the present embodiment, the plunging member guide parts are constituted by the center guide projecting part 194 and by the left and right guide plate parts 196a, 196b.

Furthermore, in the present embodiment in particular, because the left and right guide projecting parts 196a, 196b have been formed to the back side of the cover part 32 in the axial direction, when the cover part 32 is closed, the plunger 180 positioned in the pre-plunging position will be sandwiched between the left and right guide projecting parts 196a, 196b starting at the stage prior to the plunging operation. Thus, the plunger 180 will not become caught on the left or right guide projecting parts 196a, 196b, and can be guided smoothly in the axial direction, starting from the initial stage of the plunging operation.

Then, as the intraocular lens 26 is pushed along by the plunger 180, the introduction projections 192a, 192b will come into contact with the intraocular lens 26 in proximity to its center part. The intraocular lens 26 will be imparted with initial deformation thereby, allowing it to be pushed into the through-hole 72. At the same time, in the event that the working part 186 or the rod-shaped part 96 of the plunger 180 experiences displacement in the diagonal direction with respect to the axial direction of the tool body 190 due to frictional resistance or catching between the intraocular lens 26 and the through-hole 72 occurring during the plunging operation, the working part 186 or the rod-shaped part 96 will come into contact with the introduction projection 192a or 192b, thereby preventing excessive displacement of the plunger 180 in the diagonal direction. In the present embodiment in particular, because the introduction projections 192a and 192b and the left and right guide projecting parts 196a, 196b are respectively formed to either side of the stage 20 in the axial direction, excessive displacement of the plunger 180 in the horizontal direction can be limited to either side of the stage 20. Since the center guide projecting part 194 is formed extending in the axial direction, excessive displacement of the plunger 180 in the vertical direction can be limited over the entire axial extension of the stage 20. Consequently, the plunger 180 can be stably positioned across substantially the entire stage 20, and the plunging operation can take place in a more stable manner.

The specific configurations of the plunging member guide parts are not limited to the configurations described above, and any of various other configurations could be employed appropriately. For example, the center guide projecting part 194 could have a configuration extending intermittently in the axial direction. Also, the left and right guide projecting parts 196a, 196b could be formed at the axial front or in the axial medial section of the cover part 32; or the left and right guide projecting parts 196a, 196b of the preceding embodiment could be extended axially forward so as to span the entire length of the cover part 32. Additional possible configurations include forming a recessed groove extending in the axial direction in the cover part 32, with the two ends of the recessed groove substantially constituting projecting parts and the plunging member being guided by these projecting parts; or forming a recessed groove in the plunging member, forming a projection that mates with the recessed groove in the cover part 32, so that the plunging member is guided through the guiding action afforded by the recessed groove and the projection.

While not described one by one herein, other embodiments arrived at through various modifications, alterations, or improvements of the present invention will be apparent to the practitioner and as such, as a matter of course, shall lie within the true spirit and scope of this invention.

The invention claimed is:

1. An assembly comprising:
an intraocular lens insertion tool; and
an intraocular lens,
the intraocular lens insertion tool includes an tool body having a generally tubular shape adapted to accommodate the intraocular lens positioned in an enclosed state therein, and a plunging member adapted to be inserted into the tool body from behind in an axial direction so that the intraocular lens is transported forward in the axial direction while experiencing slight deformation and pushed out through an insertion tube part disposed in an axial distal end part of the tool body in order to insert the intraocular lens within an eye, wherein:
the tool body has a placement part communicating with a base end of the insertion tube part; a placement surface for placement of the intraocular lens is formed on the placement part, and at least one insertion hole is formed in the placement part at a site thereof where the placement surface has been formed; a carrying member is attached from outside the placement surface; and a plurality of support parts projected from the carrying member are passed through the insertion hole and arranged projecting up from the placement surface, with the intraocular lens being supported on projecting distal end faces of the support part, and
the intraocular lens includes a main body section having an optical region, and retaining parts that project peripherally outward from the main body section for the purpose of positioning the main body section within the eye, wherein the projecting distal end faces of the support parts contact the intraocular lens at locations away from the optical region of the main body section, with at least the one of the outside peripheral edge part of the main body section and the retaining parts being supported by the support parts.

2. The assembly according to claim 1, wherein a projecting height dimension of the support parts from the placement surface is established such that the optical region of the intraocular lens supported on the support parts will be spaced away from the placement surface.

3. The assembly according to claim 1, wherein the placement surface is defined by a flat surface.

4. The assembly according to claim 1, wherein an introduction projection extending in the axial direction of the tool body and projecting upward, and adapted to deform the intraocular lens to an upwardly convex shape relative to the placement surface, is formed in a widthwise center part of the base end of the insertion tube part.

5. The assembly according to claim 4, wherein the introduction projection is provided as a pair of elements spaced apart by a prescribed distance in a direction perpendicular to the axial direction of the tool body, and the plunging member is guided in the axial direction of the tool body by the pair of spaced apart elements.

6. The assembly according to claim 1, wherein an aperture that opens to an outer side of the tool body is formed in the placement part, and a covering part adapted to cover the aperture is integrally formed with the tool body; and a guide projection that extends in the axial direction of the tool body and, with the aperture covered by the covering part, projects to a heightwise location approximately equivalent to an inside peripheral face of the base end of the insertion tube part is formed on the covering part on a face thereof opposing the placement part.

7. The assembly according to claim 6, wherein a plunging member guide part adapted to guide the plunging member in the axial direction of the tool body is integrally formed on the covering part on the face thereof opposing the placement part.

8. The assembly according to claim 6, wherein a lubricant injection hole permitting injection of a lubricant into the tool body from the outside of the tool body is formed passing through the covering part in a direction perpendicular to a longitudinal axis of the assembly.

9. The assembly according to claim 1, wherein the tool is provided with retaining means for retaining a distal end of the plunging member in a state positioned to a rear of the placement part in the axial direction of the tool body.

10. The assembly according to claim 1, wherein a distal end edge of the plunging member is provided with a readily deformable deforming member adapted to be placed in contact against the intraocular lens.

11. The assembly according to claim 10, wherein a pair of branched parts branched in "Y" configuration are formed at the distal end edge of the plunging member; and an elastic member having hollow tubular shape is arranged bowed with both ends of the elastic member fitting about the outside of the branched parts so that a generally loop-shaped deforming member is defined by the member.

12. The assembly according to claim 1, wherein a notch is formed at a distal end of the plunging member to define a prescribed gap between the plunging member and an inside peripheral face of the insertion tube part.

13. The assembly according to claim 12, wherein the distal end of the plunging member is formed with a generally rod shape; and the notch is formed by cutting away an area somewhat to a rear of the distal end of the plunging member along a prescribed length dimension in the axial direction across an entire width of the distal end.

14. The assembly according to claim 12, wherein the distal end of the plunging member is formed with a generally rod shape; and the notch is formed by cutting away both widthwise ends of the distal end along a prescribed dimension in the axial direction from the distal end edge.

15. -An assembly according to claim 1, wherein the plurality of support parts are independently formed at respective locations of the carrying member so as to support respectively base ends and lengthwise medial sections of the retaining parts of the intraocular lens; and the at least one insertion hole comprises a plurality of insertion holes that are independently formed in the placement surface so that the independently formed support parts are inserted through the insertion holes respectively.

16. An assembly according to claim 15, wherein the support parts adapted to support the lengthwise medial sections of the retaining parts have positioning projections so that the retaining parts of the intraocular lens will extend between the positioning projections.

* * * * *